(12) United States Patent
Boyle et al.

(10) Patent No.: US 6,916,811 B2
(45) Date of Patent: Jul. 12, 2005

(54) ADENOSINE $A_{2A}$ RECEPTOR ANTAGONISTS

(75) Inventors: Craig D. Boyle, Branchburg, NJ (US); Samuel Chackalamannil, East Brunswick, NJ (US); William J. Greenlee, Teaneck, NJ (US); Unmesh G. Shah, Roselle Park, NJ (US); Yan Xia, Edison, NJ (US)

(73) Assignee: Schering Corporation, Kenilworth, NJ (US)

(*) Notice: Subject to any disclaimer, the term of this patent is extended or adjusted under 35 U.S.C. 154(b) by 91 days.

(21) Appl. No.: 10/304,931

(22) Filed: Nov. 26, 2002

(65) Prior Publication Data

US 2003/0212059 A1 Nov. 13, 2003

Related U.S. Application Data

(60) Provisional application No. 60/334,342, filed on Nov. 30, 2001.

(51) Int. Cl.[7] ............... C07D 487/04; C07D 519/00; A61K 31/519; A61P 25/18; A61P 25/16
(52) U.S. Cl. ............ 514/233; 514/257; 514/217.01; 544/115; 544/251; 540/594
(58) Field of Search ............... 544/115, 251; 514/233.2, 257

(56) References Cited

U.S. PATENT DOCUMENTS

| | | | | |
|---|---|---|---|---|
| 5,935,964 A | * | 8/1999 | Baraldi et al. | 544/251 |
| 6,407,236 B1 | * | 6/2002 | Baraldi et al. | 544/251 |
| 6,448,253 B1 | * | 9/2002 | Baraldi | 544/251 |
| 6,630,475 B2 | * | 10/2003 | Neustadt et al. | 514/257 |
| 2003/0144266 A1 | * | 7/2003 | Baraldi et al. | 544/251 |
| 2004/0023997 A1 | * | 2/2004 | Neustadt et al. | 514/267 |
| 2004/0039004 A1 | * | 2/2004 | Baraldi et al. | 544/251 |
| 2004/0220194 A1 | * | 11/2004 | Neustadt et al. | 544/251 |

FOREIGN PATENT DOCUMENTS

| | | | | |
|---|---|---|---|---|
| EP | 0 856 003 | 8/1998 | | |
| WO | WO 95/01356 | 1/1995 | ......... | C07D/487/14 |
| WO | WO 98/52568 | 11/1998 | ......... | A61K/31/495 |
| WO | WO 00/15231 | 3/2000 | ......... | A61K/31/505 |
| WO | WO 01/92264 A1 | 12/2001 | ......... | C07D/487/14 |

OTHER PUBLICATIONS

Pecherer et al, *J. Hetero. Chem.*, 8 (1971), p. 779–783.
Shiozawa et al, *Chem. Pharm. Bull.*, 32 (1984), p. 2522–2529.
Ungersatdt et al, *Brain Research*, 24 (1970), p. 485–93.
Ungerstadt, *Eur. J. Pharmacol.*, 5 (1968), p. 107–110.
Pier Giovanni Baraldi et al., Pyrazolo[4,3-e]-1,2,4-triazolo [1,5-c]pyrimidine Derivatives: Potent and Selective $A_{2A}$ Adenosine Antagonists, J. Med. Chem., 1996, 39(5), 1164–1171.
Camille G. Wermuth, Molecular Variations Based on Isosteric Replacements, The Practice of Medicinal Chemistry, 1996, XP–002190259, 203–237.

* cited by examiner

Primary Examiner—Mark L. Berch
(74) Attorney, Agent, or Firm—Anita W. Magatti

(57) ABSTRACT

Disclosed herein are compounds having the structural formula A

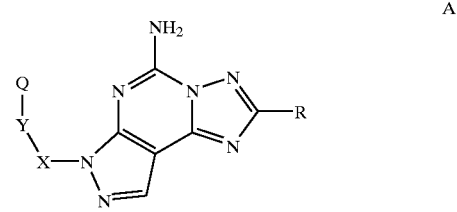

including pharmaceutically acceptable salts or solvates of said compound, wherein X, Y, Q and R are as defined in the specification; pharmaceutical compositions thereof; methods of treating central nervous system diseases by administering the compound of the present invention to a patient in need of such treatment, and processes for preparing the compound of this invention.

9 Claims, No Drawings

ADENOSINE $A_{2A}$ RECEPTOR ANTAGONISTS

CROSS REFERENCE TO RELATED APPLICATION

This application claims priority to U.S. Provisional Application No. 60/334,342, filed Nov. 30, 2001.

BACKGROUND

This invention relates to adenosine $A_{2a}$ receptor antagonists, the use of said compounds in the treatment of central nervous system diseases, in particular Parkinson's disease, and to pharmaceutical compositions comprising said compounds. The invention also relates to a process for preparing the pyrimidine derivatives of the present invention.

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. $A_1$ and $A_3$ are high-affinity, inhibiting the activity of the enzyme adenylate cyclase, and $A_{2a}$ and $A_{2b}$ are low-affinity, stimulating the activity of the same enzyme. Analogs of adenosine able to interact as antagonists with the $A_1$, $A_{2a}$, $A_{2b}$ and $A_3$ receptors have also been identified.

Selective antagonists for the $A_{2a}$ receptor are of pharmacological interest because of their reduced level of side affects. In the central nervous system, $A_{2a}$ antagonists can have antidepressant properties and stimulate cognitive functions. Moreover, data has shown that $A_{2a}$ receptors are present in high density in the basal ganglia, known to be important in the control of movement. Hence, $A_{2a}$ antagonists can improve motor impairment due to neurodegenerative diseases such as Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2a}$ affinity with varying degrees of $A_{2a}$ vs. $A_1$ selectivity. Triazolo-pyrimidine adenosine $A_{2a}$ receptor antagonists with different substitution at the 7-position have been disclosed previously, for example in WO 95/01356; U.S. Pat. No. 5,565,460; WO 97/05138; and WO 98/52568.

SUMMARY OF THE INVENTION

This invention relates to compounds having the structural formula A

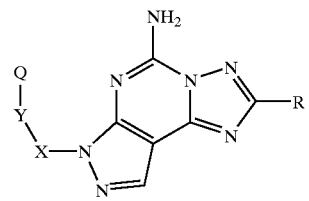

or a pharmaceutically acceptable salt or solvate of said compound, wherein:

R is selected from the group consisting of $R^1$-furanyl-, $R^1$-thienyl-, $R^1$-pyridyl-, $R^1$-oxazolyl-, $R^1$-pyrrolyl- and $R^2$-aryl-;

X is —$(CH_2)_n$—;

Y is a piperidinyl, pyrrolidinyl or azepanyl group with an aryl or heteroaryl moiety fused to two adjacent carbon atoms on Y, wherein X is attached to the N atom of the piperidinyl, pyrrolidinyl or azepanyl group;

Q is 1–4 substituents, which can be the same or different, and are independently selected from the group consisting of hydrogen, cycloalkyl, cycloheteroalkyl, amino, aryl, aralkyl, heteroaryl, alkyl, $CF_3$, halogen, $NO_2$, alkoxy, alkoxyalkoxy, cycloalkylalkoxy, acyloxy, alkylamino, acylamino, alkylsulfonamino, alkylaminosulfonyl, dialkylaminosulfonyl, —$NH_2SO_2$—, and hydroxy;

n is 1 to 4;

$R^1$ is 1–3 substituents, which may be the same or different, and are independently selected from the group consisting of hydrogen, alkyl, $CF_3$, halogen and $NO_2$; and $R^2$ is 1–3 substituents, which may be the same or different, and are independently selected from the group consisting of hydrogen, alkyl, —$CF_3$, halogen, $NO_2$, alkoxy, acyloxy, alkylamino, acylamino, alkylsulfonamido, alkylaminosulfonyl, dialkylaminosulfonyl, aminosulfonyl, and hydroxyl.

In a preferred embodiment, Y is

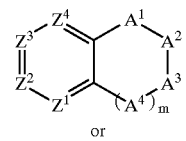

or

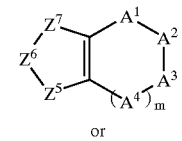

or

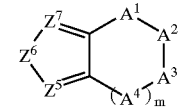

wherein $A^1$ is N—X, and $A^2$ and $A^3$ each are $CR^4R^5$, or $A^1$ and $A^3$ each are $CR^4R^5$, and $A^2$ is N—X, or $A^1$ and $A^2$ each are $CR^4R^5$, and $A^3$ is N—X;

$A^4$ is $CR^4R^5$;

$Z^1$, $Z^2$, $Z^3$ and $Z^4$, which can the same or different, are each independently selected from the group consisting of N and $CR^3$, provided that 0–2 of $Z^1$, $Z^2$, $Z^3$ or $Z^4$ are N and the remainder are $CR^3$;

$Z^5$ is $NR^5$, O, S or $CR^4R^5$;

$Z^6$ is N or $CR^3$;

$Z^7$ is N or $CR^3$;

m is an integer from 0 to 2;

$R^3$ is selected from the group consisting of hydrogen, cycloalkyl, amino, aryl, heteroaryl, $C_1$–$C_6$-alkyl, $CF_3$, halogen, $NO_2$, $C_1$–$C_6$-alkoxy, $C_1$–$C_6$-acyloxy, $C_1$–$C_6$-alkylamino, $C_1$–$C_6$-acylamino, $C_1$–$C_6$-alkylsulfonamino, $C_1$–$C_6$-alkylaminosulfonyl, $C_1$–$C_6$-dialkylaminosulfonyl, aminosulfonyl, and hydroxy;

$R^4$ is selected from the group consisting of hydrogen, hydroxyalkyl, aryl, aralkyl, $C_1$–$C_6$-alkyl, $C_1$–$C_6$-alkoxy, —$CF_3$, halogen, hydroxy, and $NO_2$; and $R^5$ is hydrogen or $C_1$–$C_6$ alkyl.

Another aspect of the invention relates to a pharmaceutical composition comprising one or more compounds of formula A, preferably with one or more pharmaceutically acceptable carriers. Preferably, the pharmaceutical composition comprises a therapeutically effective amount of one or more compounds of formula A.

Another aspect of the invention relates to a pharmaceutical composition comprising one or more compounds of formula A in combination or association with one or more agents known to be useful in the treatment of Parkinson's disease, preferably with one or more pharmaceutically acceptable carriers. Preferably, the pharmaceutical composition comprises a therapeutically effective amount of one or more compounds of formula A.

Another aspect of the invention relates to a method of treating central nervous system diseases such as depression, cognitive diseases and neurodegenerative diseases such as Parkinson's disease, senile dementia or psychoses of organic origin, or stroke, comprising administering one or more compounds of formula A to a patient in need of such treatment. Preferably the method is drawn to treating Parkinson's disease comprising administering one or more compounds of formula A to a patient in need of such treatment. Preferably, the amount of one or more compounds of formula A administered is a therapeutically effective amount of one or more compounds of formula A.

Another aspect of the invention relates to a method of treating Parkinson's disease comprising administering to a patient in need of such treatment a combination or association of one or more compounds of formula A and one or more agents useful in the treatment of Parkinson's disease, for example dopamine, a dopaminergic agonist; an inhibitor of monoamine oxidase, type B (MAO-B), a DOPA decarboxylase inhibitor (DCI), or a catechol-O-methyltransferase (COMT) inhibitor. Preferably, the amount of one or compounds of formula A administered is a therapeutically effective amount of one or more compounds of formula A. In this aspect of the invention, one or more compounds of formula A and one or more other anti-Parkinson's agents can be administered simultaneously, concurrently or sequentially in separate dosage forms.

Yet, another aspect of the invention relates to a kit comprising a pharmaceutical compositions for use in combination to treat Parkinson's disease, wherein said composition comprises one or more compounds of formula A, one or more pharmaceutically acceptable carriers, and one or more agents useful in the treatment of Parkinson's disease.

DETAILED DESCRIPTION

This invention relates to compounds having the structural formula A

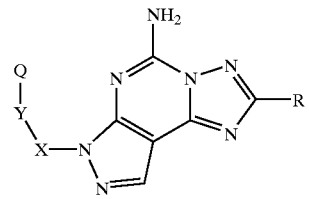

wherein R, X, Y and Q are as defined above.

In a preferred embodiment, Y is

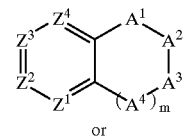

or

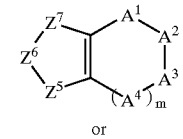

or

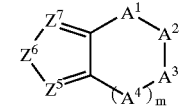

wherein $A^1$ is N—X, and $A^2$ and $A^3$ each are $CR^4R^5$, or $A^1$ and $A^3$ each are $CR^4R^5$, and $A^2$ is N—X, or $A^1$ and $A^2$ each are $CR^4R^5$, and $A^3$ is N—X;

$A^4$ is $CR^4R^5$;

$Z^1$, $Z^2$, $Z^3$ and $Z^4$, which can the same or different, are each independently selected from the group consisting of N and $CR^3$, provided that 0–2 of $Z^1$, $Z^2$, $Z^3$ or $Z^4$ are N and the remainder are $CR^3$;

$Z^5$ is $NR^5$, O, S or $CR^4R^5$;

$Z^6$ is N or $CR^3$;

$Z^7$ is N or $CR^3$;

m is an integer from 0 to 2;

$R^3$ is selected from the group consisting of hydrogen, cycloalkyl, amino, aryl, heteroaryl, $C_1$–$C_6$-alkyl, $CF_3$, halogen, $NO_2$, $C_1$–$C_6$-alkoxy, $C_1$–$C_6$-acyloxy, $C_1$–$C_6$-alkylamino, $C_1$–$C_6$-acylamino, $C_1$–$C_6$-alkylsulfonamino, $C_1$–$C_6$-alkylaminosulfonyl, $C_1$–$C_6$-dialkylaminosulfonyl, aminosulfonyl, and hydroxy;

$R^4$ is selected from the group consisting of hydrogen, hydroxyalkyl, aryl, aralkyl, $C_1$–$C_6$-alkyl, $C_1$–$C_6$-alkoxy, —$CF_3$, halogen, hydroxy, and $NO_2$; and $R^5$ is hydrogen or $C_1$–$C_6$ alkyl.

As used herein, the following terms are used as defined below unless otherwise indicated.

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

Heteroaryl means a single ring, bicyclic or benzofused heteroaromatic group of 5 to 10 atoms comprised of 1 to 9 carbon atoms and 1 to 4 heteroatoms independently selected from the group consisting of N, O and S, provided that the rings do not include adjacent oxygen and/or sulfur atoms. The carbon atoms or heteroatoms can be optionally substituted. N-oxides of the ring nitrogens are also included. Examples of single-ring heteroaryl groups are pyridyl, oxazolyi, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1, 5 or 1,7), imidazopyridyl, pyrido[2,3]imidazolyl, pyridopyrimidinyl and 7-azaindolyl. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 2-pyridyl, 3-pyridyl and 4-pyridyl.

The term "optionally substituted" means optional substitution with the specified groups, radicals or moieties.

The term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula A or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" as used herein means an amount sufficient to treat central nervous system diseases such as depression, cognitive diseases and neurodegenerative diseases such as Parkinson's disease, senile dementia and psychoses of organic origin. Preferably, the therapeutically effective amount of active compound in a unit dose of preparation can range from about 0.1 mg to about 1000 mg, more preferably from about 1 mg to about 300 mg.

The compounds of formula A form salts which are also within the scope of this invention. Reference to a compound of formula A herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula A contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., nontoxic, physiologically acceptable) salts are preferred, although other salts are also useful. Salts of the compounds of the formula A may be formed, for example, by reacting a compound of formula A with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula A, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prod rugs of the inventive compounds.

Non-limiting examples of compounds of the present invention include, but are not limited to, compounds selected from the group consisting of

| COMPOUND # | STRUCTURE |
|---|---|
| 1 | 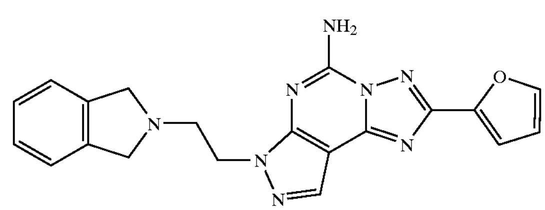 |
| 2 | 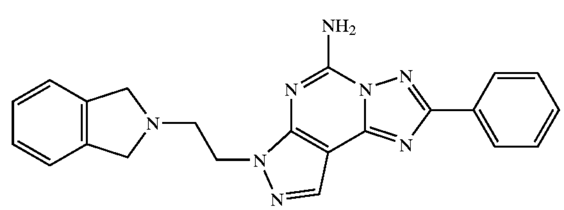 |

-continued

| COMPOUND # | STRUCTURE |
|---|---|
| 3 | 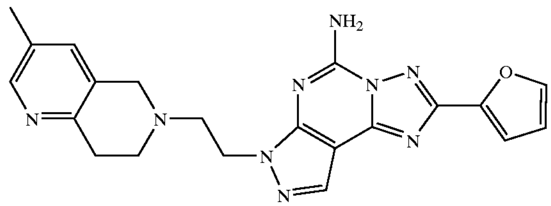 |
| 4 | 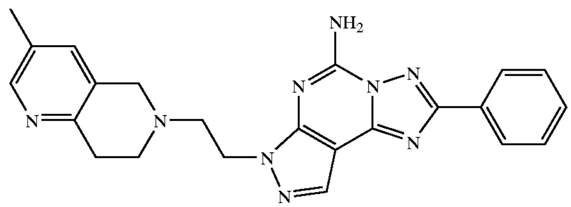 |
| 5 | 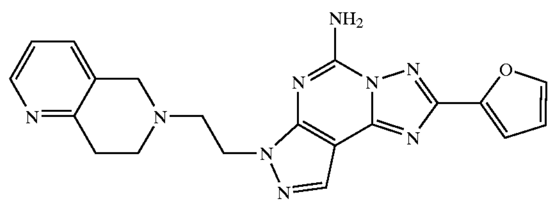 |
| 6 | 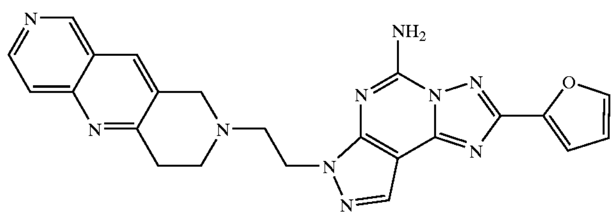 |
| 7 | 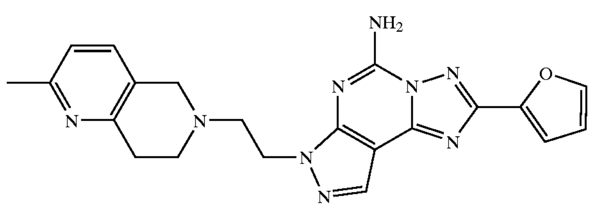 |
| 8 | 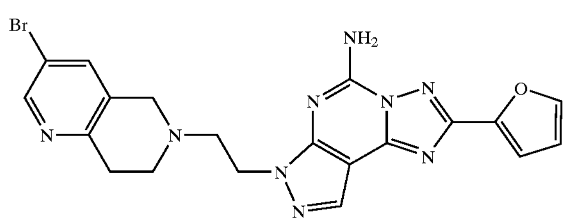 |
| 9 | 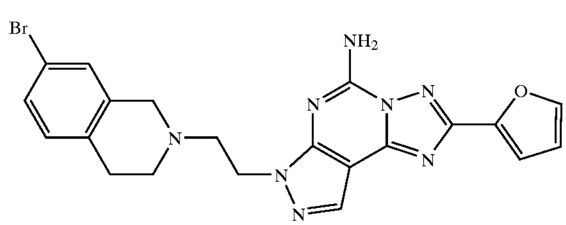 |

-continued
| COMPOUND # | STRUCTURE |
|---|---|
| 10 | 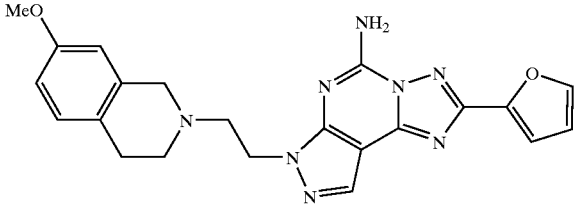 |
| 11 | 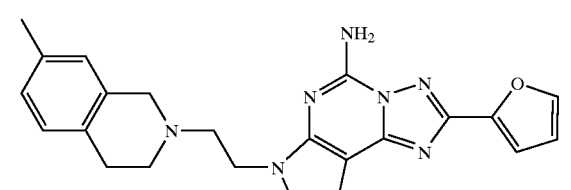 |
| 12 | 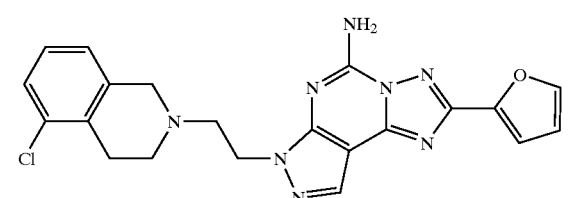 |
| 13 | 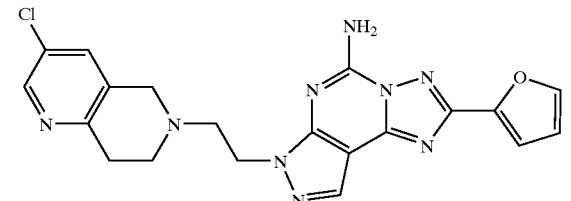 |
| 14 | 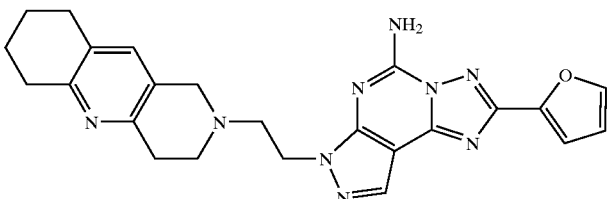 |
| 15 | 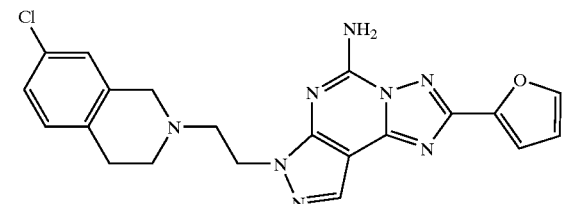 |
| 16 | 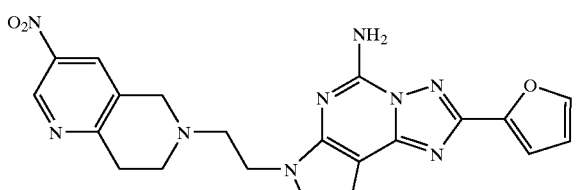 |

-continued

| COMPOUND # | STRUCTURE |
|---|---|
| 17 | 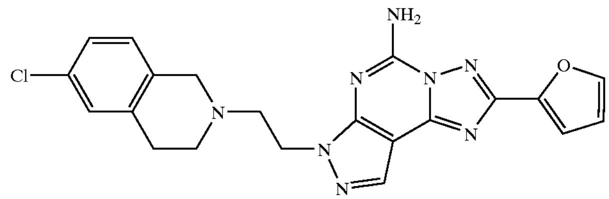 |
| 18 | 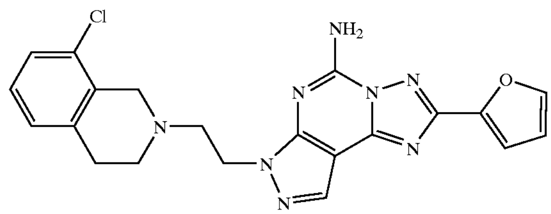 |
| 19 | 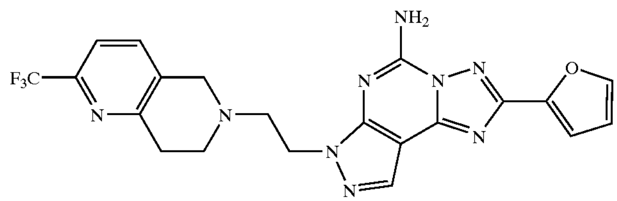 |
| 20 | 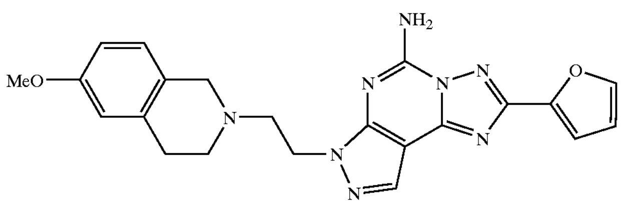 |
| 21 | 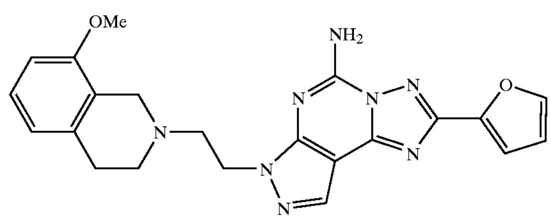 |
| 22 | 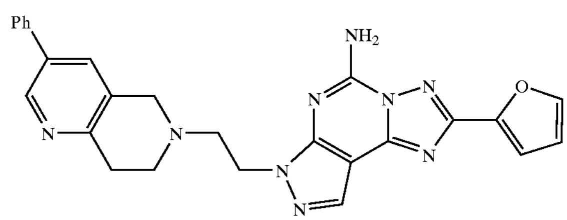 |
| 23 | 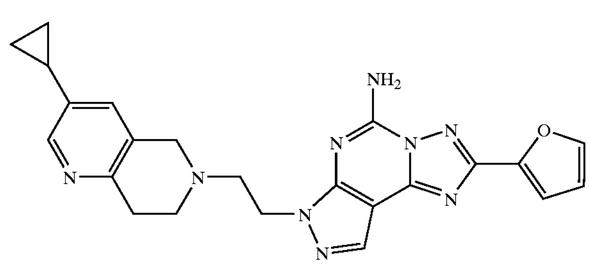 |

-continued

| COMPOUND # | STRUCTURE |
|---|---|
| 24 | 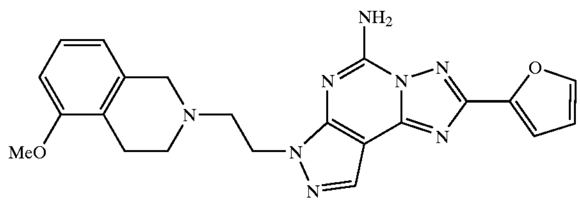 |
| 25 | 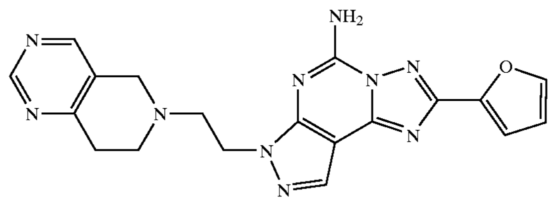 |
| 26 | 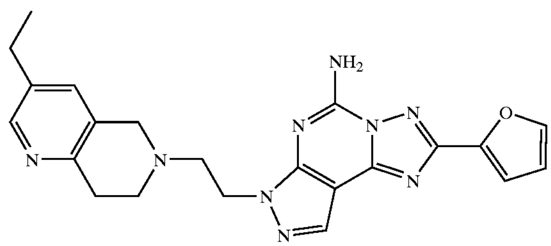 |
| 27 | 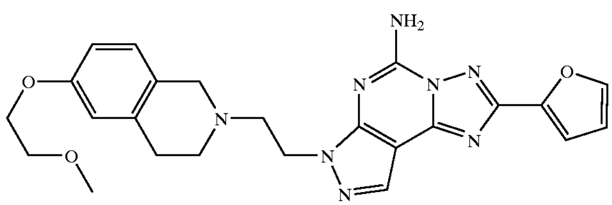 |
| 28 | 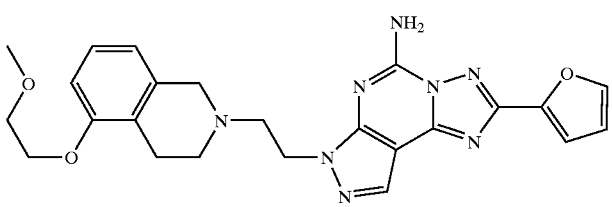 |
| 29 | 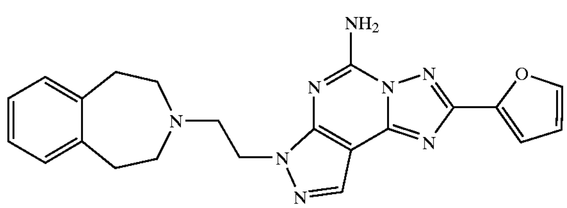 |
| 30 | 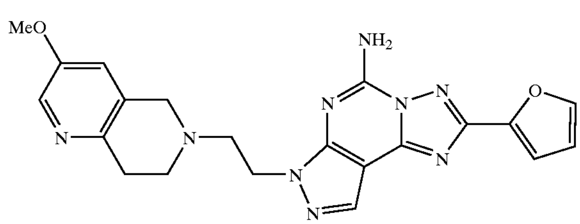 |

-continued
| COMPOUND # | STRUCTURE |
|---|---|
| 31 | 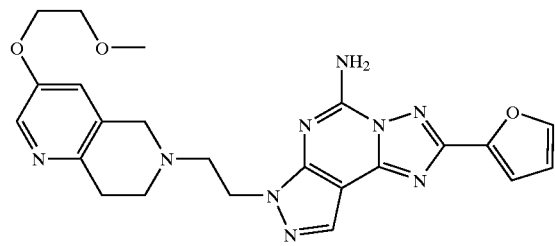 |
| 32 | 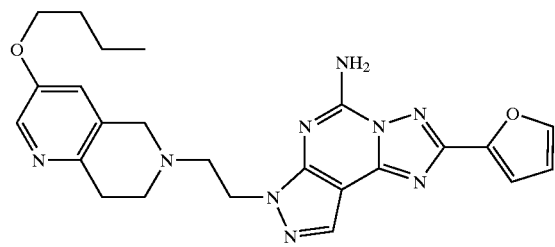 |
| 33 | 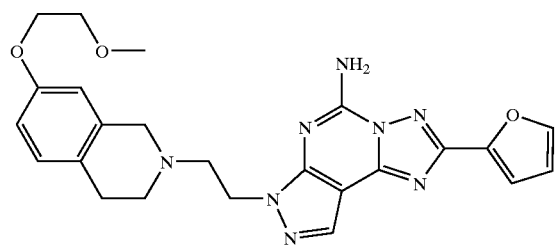 |
| 34 | 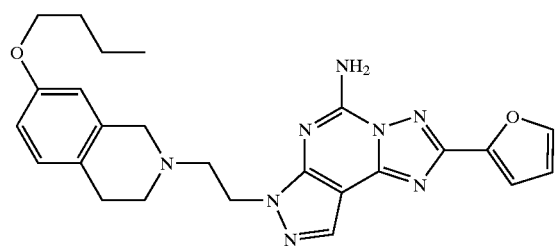 |
| 35 | 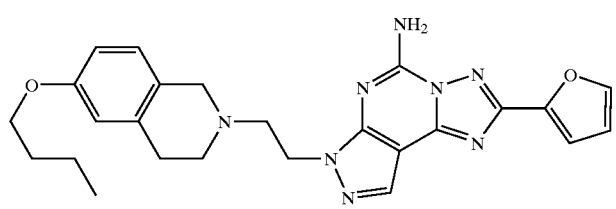 |
| 36 | 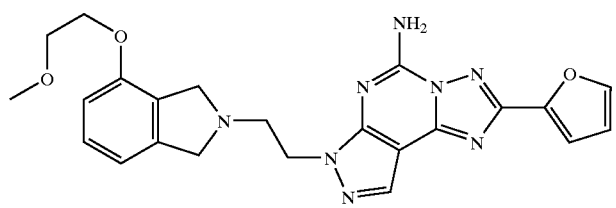 |

-continued

| COMPOUND # | STRUCTURE |
| --- | --- |
| 37 | 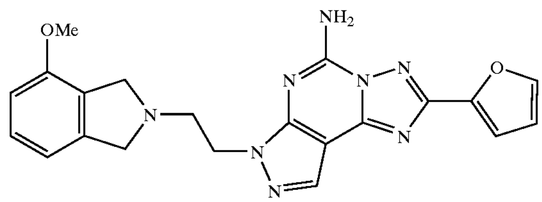 |
| 38 | 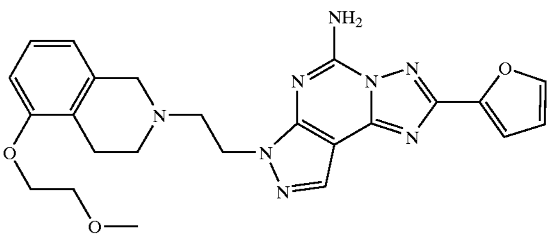 |
| 39 | 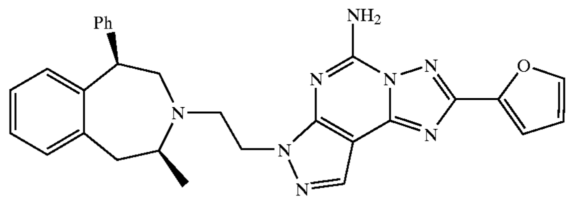 |
| 40 | 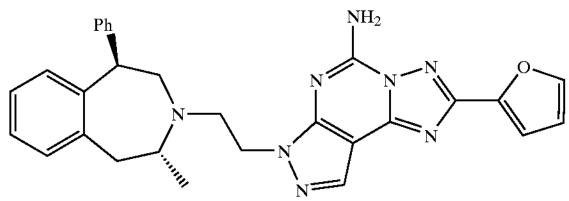 |
| 41 | 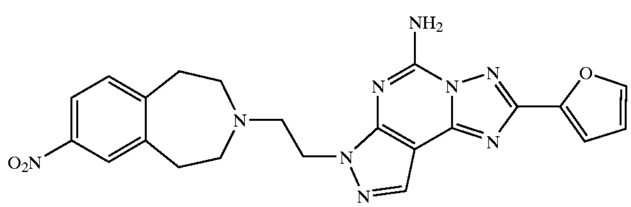 |
| 42 | 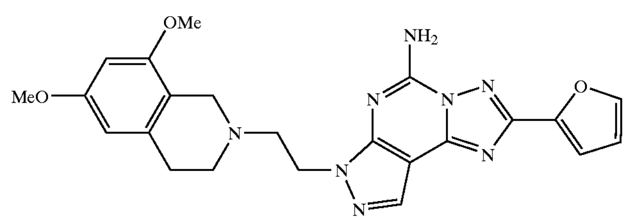 |
| 43 | 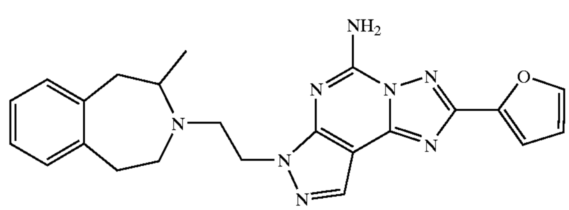 |

-continued

| COMPOUND # | STRUCTURE |
|---|---|
| 44 | (structure) |
| 45 | (structure) |
| 46 | (structure) |
| 47 | (structure) |
| 48 | (structure) |
| 49 | (structure) |
| 50 | (structure) |

-continued

| COMPOUND # | STRUCTURE |
|---|---|
| 51 | 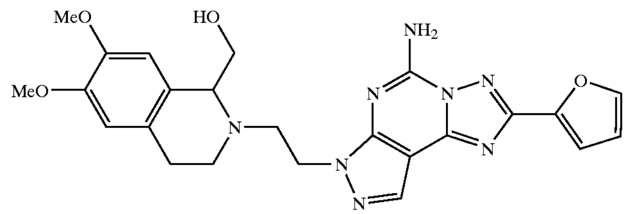 |
| 52 | 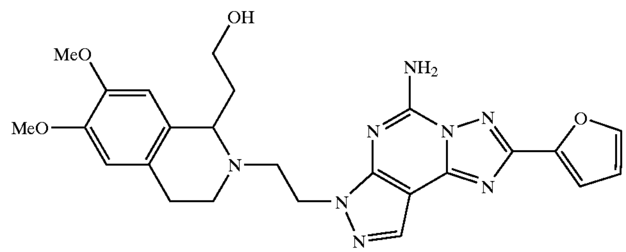 |
| 53 | 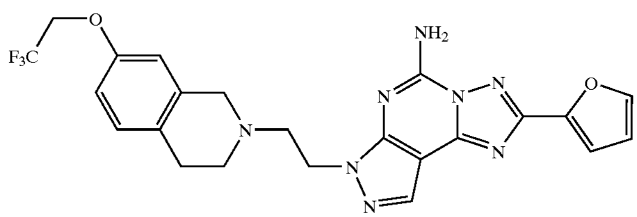 |
| 54 | 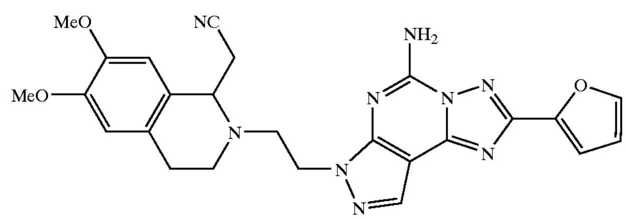 |
| 55 | 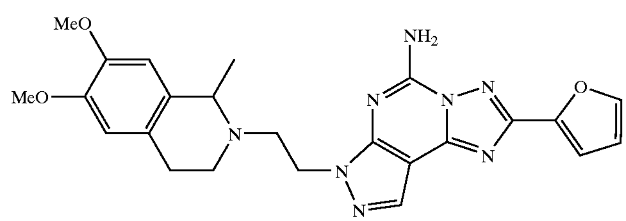 |
| 56 | 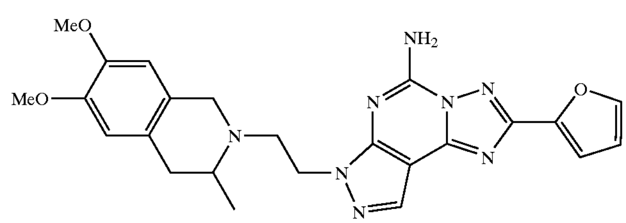 |
| 57 | 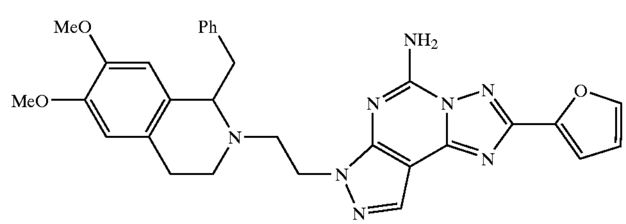 |

-continued
| COMPOUND # | STRUCTURE |
| --- | --- |
| 58 | 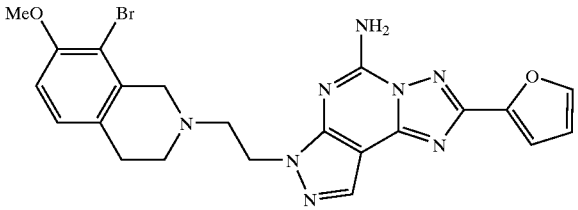 |
| | AND |
| 59 | 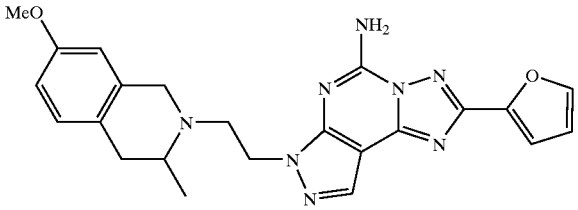 |
In a preferred embodiment, the compounds of the present invention have an $A_{2a}$ $K_i$ of $\leq 20$ nM, and an $A_1/A_{2a}$ of $\geq 40$.
Non-limiting examples of compounds in this embodiment include compounds selected from the group consisting of
| COMPOUND # | STRUCTURE |
| --- | --- |
| 1 | 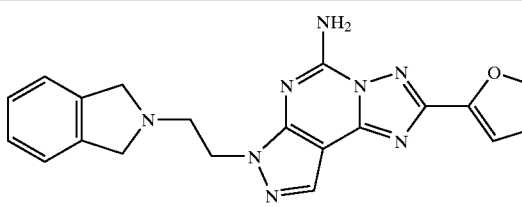 |
| 3 | 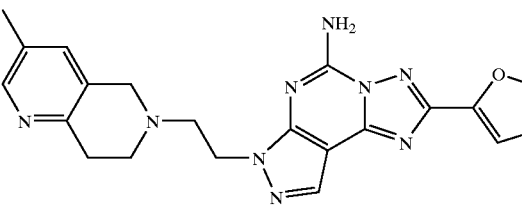 |
| 5 | 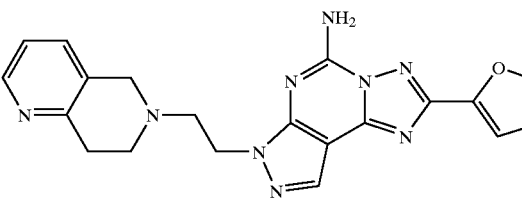 |
| 6 | 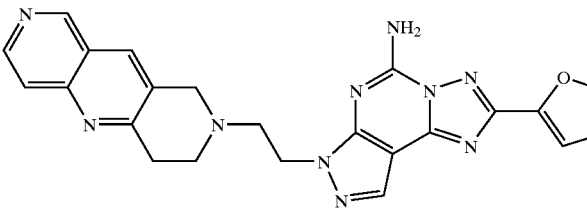 |

-continued

| COMPOUND # | STRUCTURE |
|---|---|
| 7 | 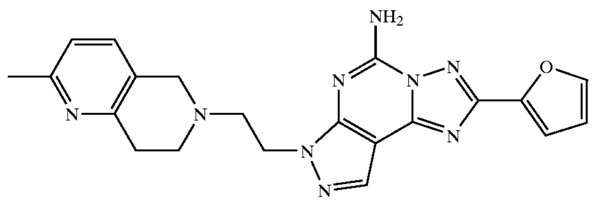 |
| 8 | 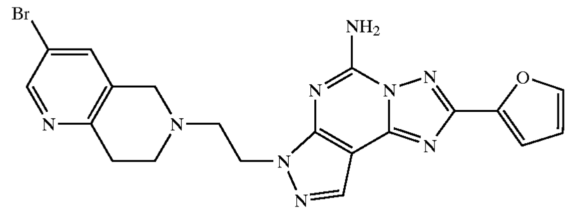 |
| 9 | 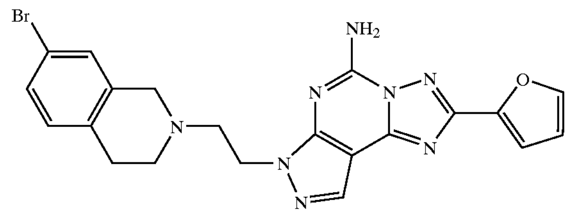 |
| 10 | 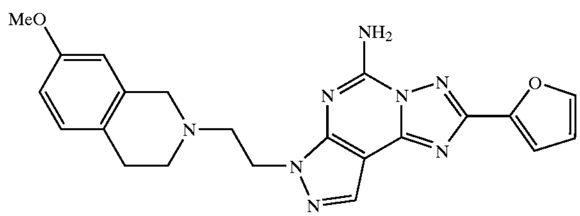 |
| 20 | 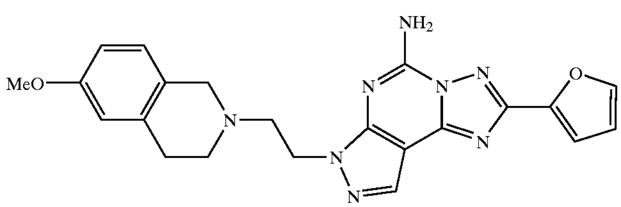 |
| 21 | 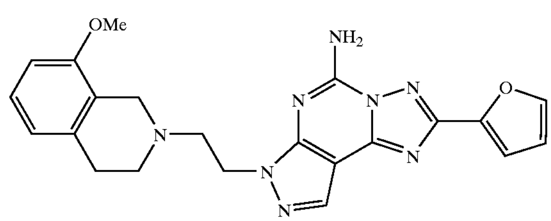 |
| 23 | 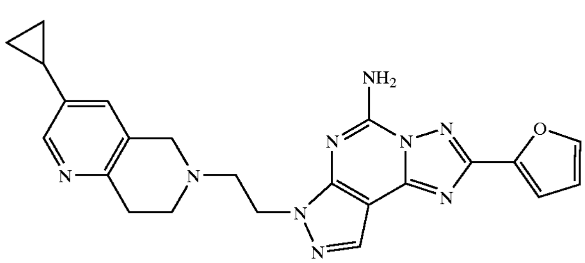 |

-continued

| COMPOUND # | STRUCTURE |
|---|---|
| 27 | 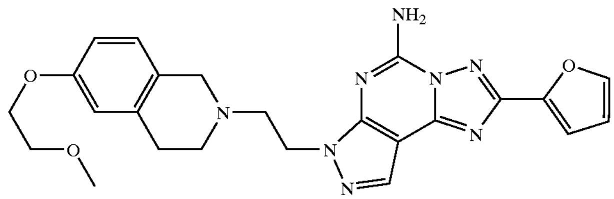 |
| 28 | 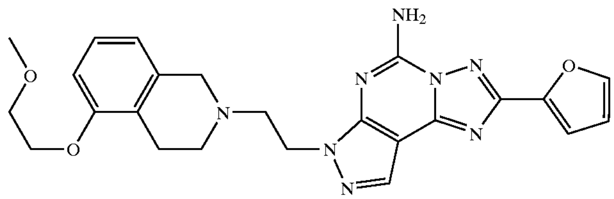 |
| 29 | 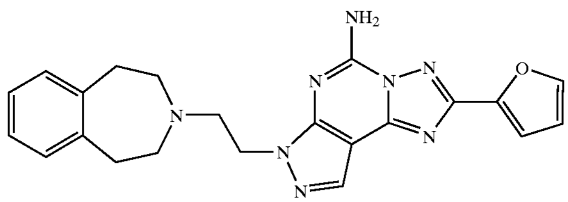 |
| 30 | 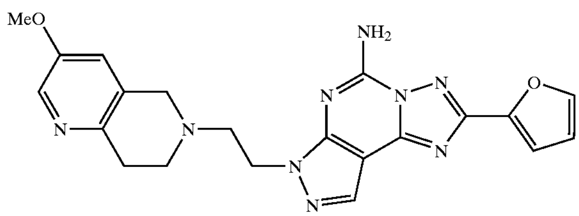 |
| 31 | 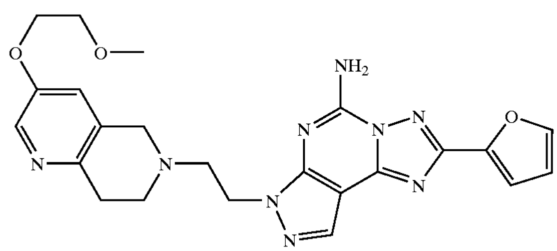 |
| 33 | 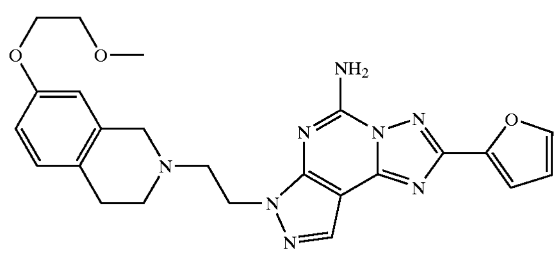 |
| 35 | 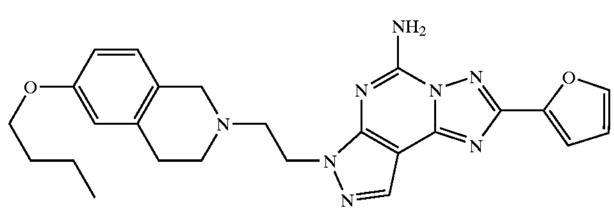 |

-continued
| COMPOUND # | STRUCTURE |
|---|---|
| 36 | 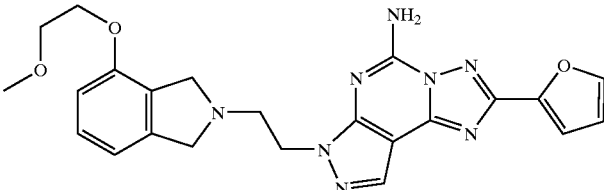 |
| 37 | 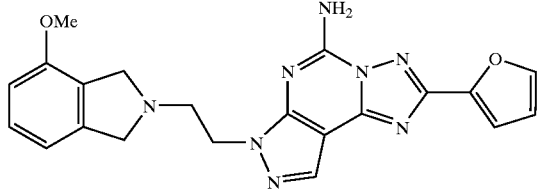 |
| 38 | 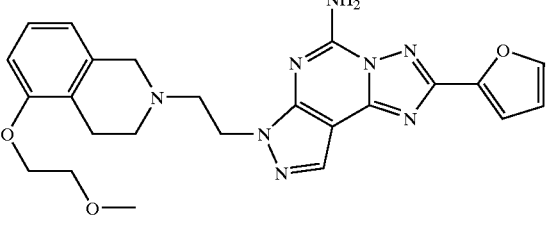 |
| 41 | 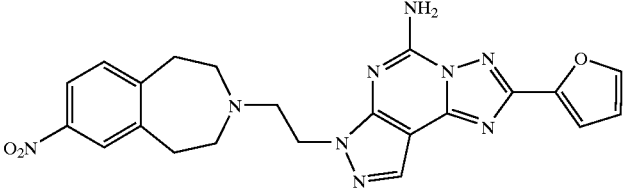 |
| 42 | 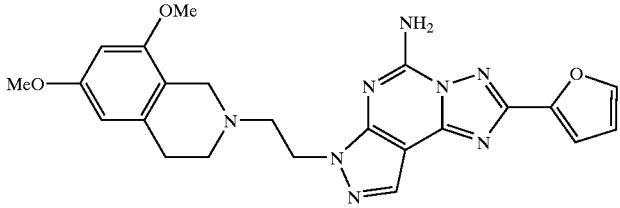 |
| 44 | 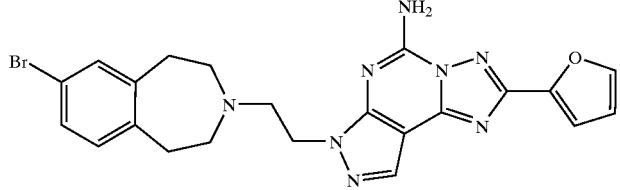 |
| 47 | 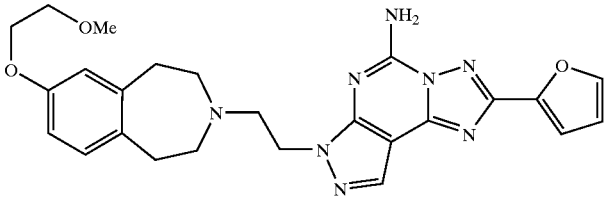 |

-continued

| COMPOUND # | STRUCTURE |
|---|---|
| 48 | 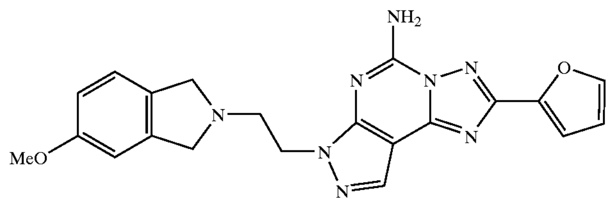 |
| 49 | 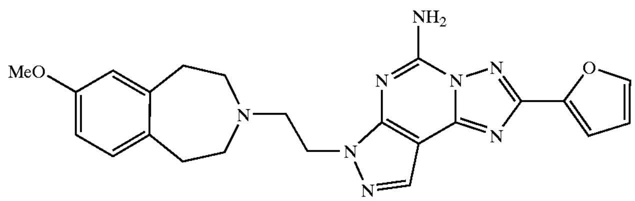 |
| 51 | 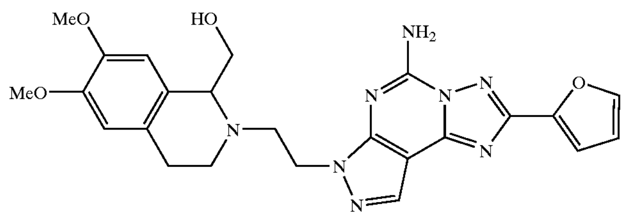 |
| 54 | 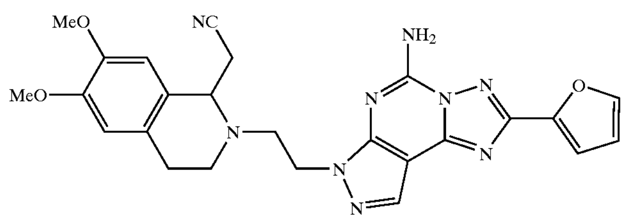 |
| 55 | 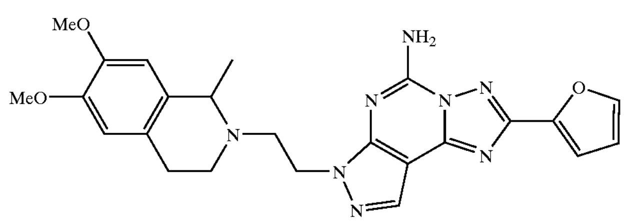 |
| 56 | 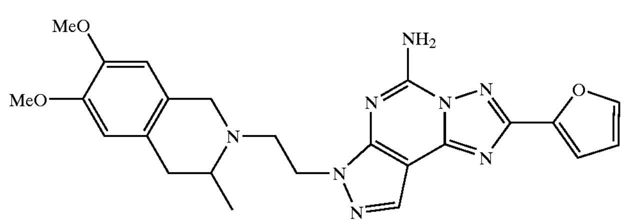 |
| 57 | 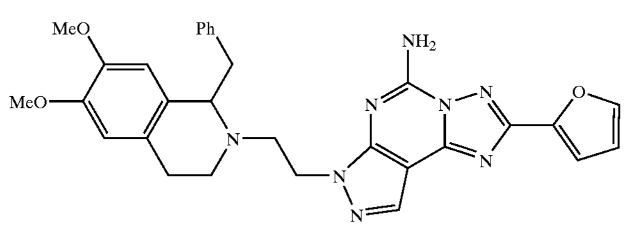 |

| COMPOUND # | STRUCTURE |
|---|---|
| 58 | 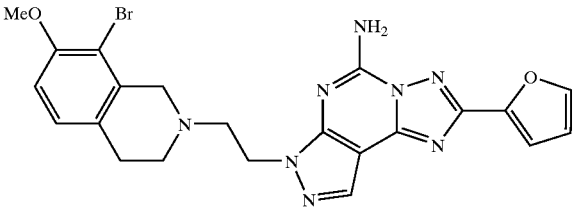 |
| | AND |
| 59 | 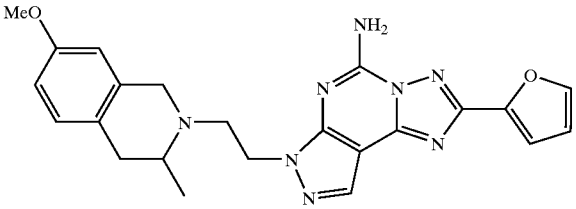 |
In a more preferred embodiment, the compounds of the present invention have an $A_{2a}$ $K_i$ of $\leq 10$ nM, and an $A_1/A_{2a}$ of $\geq 80$. Non-limiting examples of compounds in this embodiment include compounds selected from the group consisting of
| COMPOUND # | STRUCTURE |
|---|---|
| 3 | 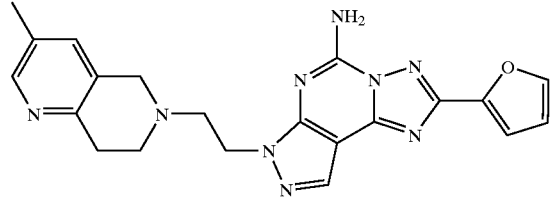 |
| 7 | 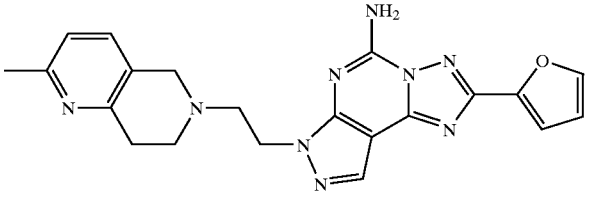 |
| 28 | 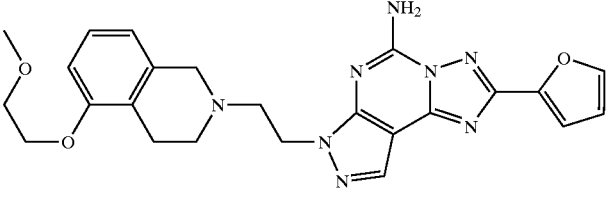 |
| 29 | 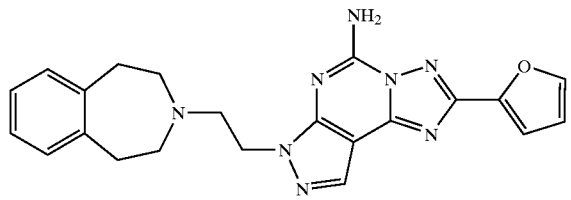 |

-continued

| COMPOUND # | STRUCTURE |
|---|---|
| 31 | 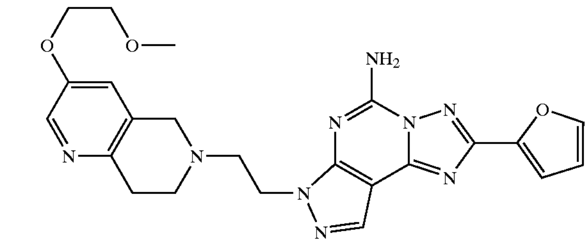 |
| 35 | 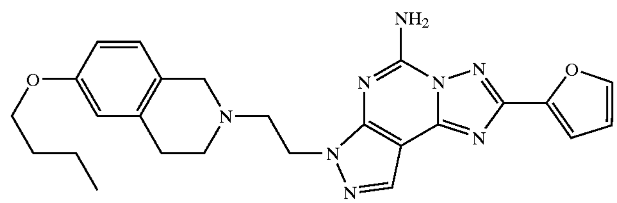 |
| 36 | 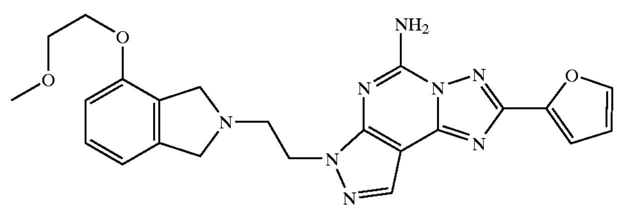 |
| 37 | 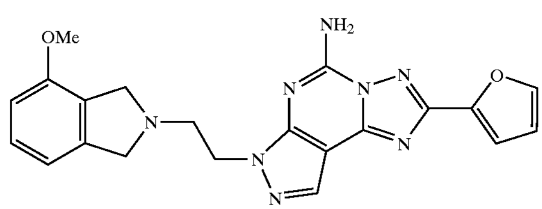 |
| 42 | 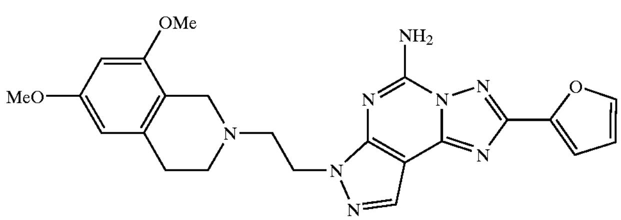 |
| 47 | 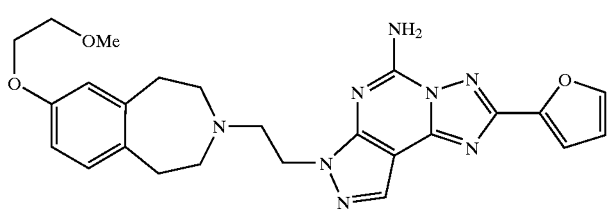 |
| 48 | 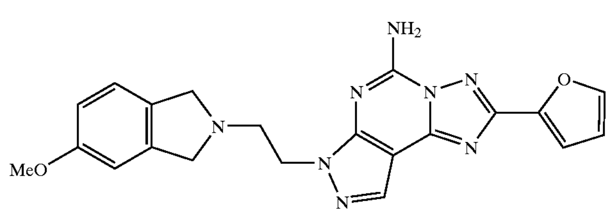 |

-continued

| COMPOUND # | STRUCTURE |
|---|---|
| 49 | 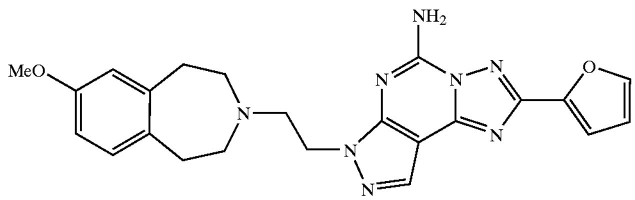 |
| 51 | 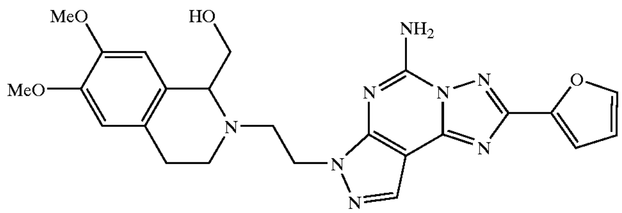 |
| 56 | 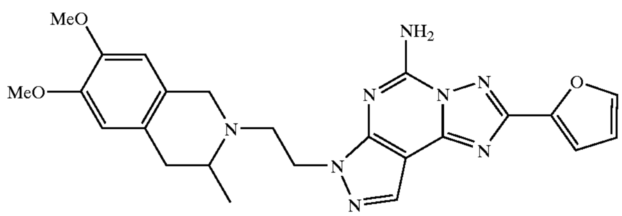 |
| | AND |
| 57 | 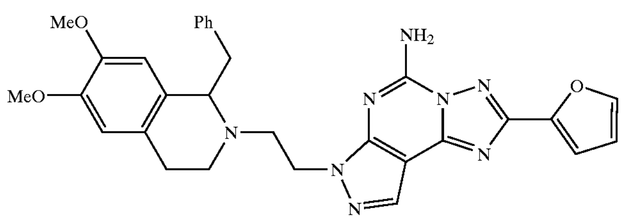 |

In an even more preferred embodiment, the compounds of the present invention have an $A_{2a}$ $K_i$ of $\leq 5$ nM, and an $A_1/A_{2a}$ of $\geq 100$. Non-limiting examples of compounds in this embodiment include compounds selected from the group consisting of

| COMPOUND # | STRUCTURE | $A_{2a}$ $K_i$ (nM) | $A_1/A_{2a}$ |
|---|---|---|---|
| 3 | 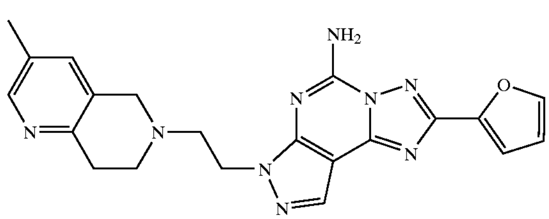 | 2.0 | 179 |

-continued

| COMPOUND # | STRUCTURE | $A_{2a}$ $K_i$ (nM) | $A_1/A_{2a}$ |
|---|---|---|---|
| 29 | 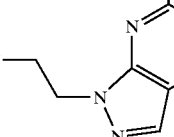 | 2.0 | 215 |
| 47 | 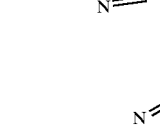 | 2.0 | 306 |
| 49 | 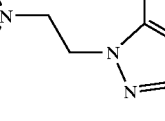 | 1.9 | 463 |
| 56 | 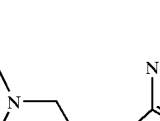 | 1.9 | 149 |
| | AND | | |
| 57 | 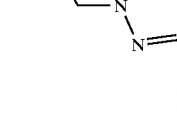 | 2.3 | 146 |

These compounds possess antagonistic activity at $A_{2a}$ receptors and are useful in the treatment of Parkinson's disease and depression. They may be used alone, in combination or in association with dopaminergic agents such as L-DOPA or ropinrole. They may also be used in conjunction with known anti-depressant therapeutic agents.

Another aspect of the invention relates to a pharmaceutical composition comprising one or more compounds of formula A, preferably with one or more pharmaceutically acceptable carriers. Preferably, the pharmaceutical composition comprises a therapeutically effective amount of one or more compounds of formula A.

Another aspect of the invention relates to a pharmaceutical composition comprising one or more compounds of formula A in combination or association with one or more agents known to be useful in the treatment of Parkinson's disease, preferably with one or more pharmaceutically acceptable carriers. Preferably, the pharmaceutical composition comprises a therapeutically effective amount of one or more compounds of formula A.

Another aspect of the invention relates to a method of treating central nervous system diseases such as depression, cognitive diseases and neurodegenerative diseases such as Parkinson's disease, senile dementia or psychoses of organic origin, or stroke, comprising administering one or more compounds of formula A to a patient in need of such treatment. Preferably the method is drawn to treating Parkinson's disease comprising administering one or more compounds of formula A to a patient in need of such treatment. Preferably, the amount of one or more compounds of formula A administered is a therapeutically effective amount of one or more compounds of formula A.

Another aspect of the invention relates to a method of treating Parkinson's disease comprising administering to a patient in need of such treatment a combination or association of one or more compounds of formula A and one or more agents useful in the treatment of Parkinson's disease, for example dopamine, a dopaminergic agonist; an inhibitor of monoamine oxidase, type B (MAO-B), a DOPA decarboxylase inhibitor (DCI), or a catechol-O-methyltransferase (COMT) inhibitor. Preferably, the amount of one or compounds of formula A administered is a therapeutically effective amount of one or more compounds of formula A. In this aspect of the invention, one or more compounds of formula A and one or more other anti-Parkinson's agents can be administered simultaneously, concurrently or sequentially in separate dosage forms.

Yet, another aspect of the invention relates to a kit comprising a pharmaceutical compositions for use in combination to treat Parkinson's disease, wherein said composition comprises one or more compounds of formula A, one or more pharmaceutically acceptable carriers, and one or more agents useful in the treatment of Parkinson's disease.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired. The amount and frequency of administration of the compounds of the invention and the pharmaceutically acceptable salts thereof will be regulated according to the judgment of the attending clinician considering such factors as age, condition and size of the patient as well as severity of the symptoms being treated.

The compounds of formula A are prepared by the methods shown in the following reaction schemes:

SCHEME 1

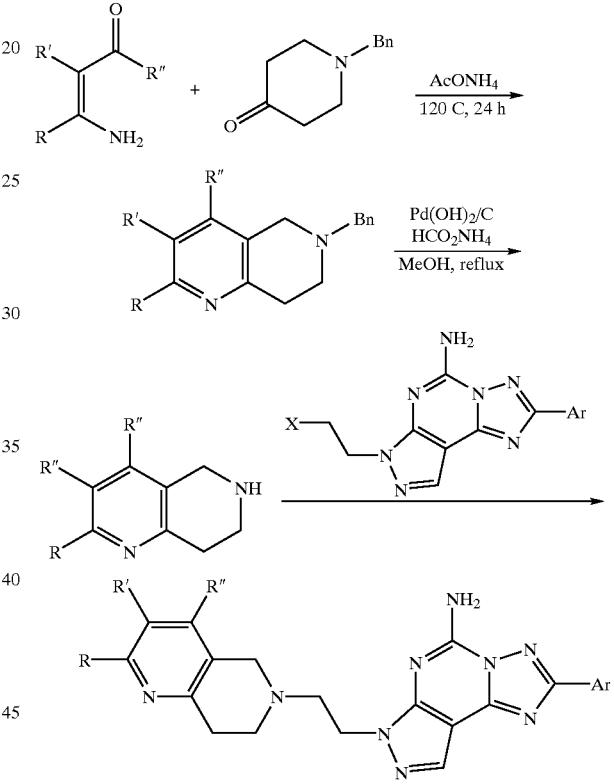

Benzyl piperidinone is cyclized with an aminoacrylaldehyde to form the benzyl protected tetrahydronaphthyridine. Hydrogenolysis followed by displacement of a leaving group provides the desired final product.

SCHEME 2

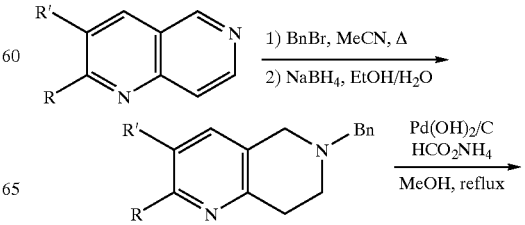

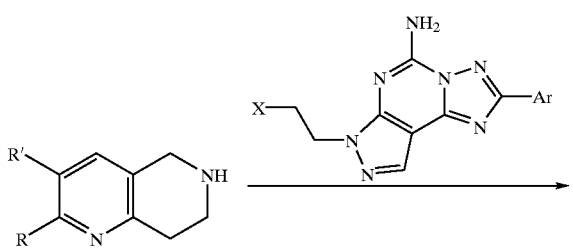

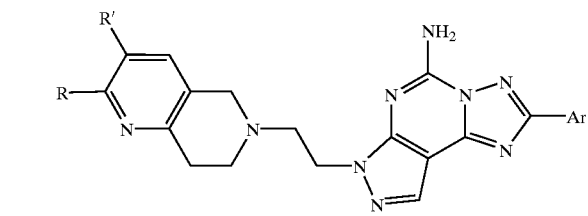

Quaternization of a naphthyridine followed by reduction gives a benzyl protected tetrahydronaphthyridine. Hydrogenolysis followed by displacement of a leaving group provides the desired final product.

SCHEME 3

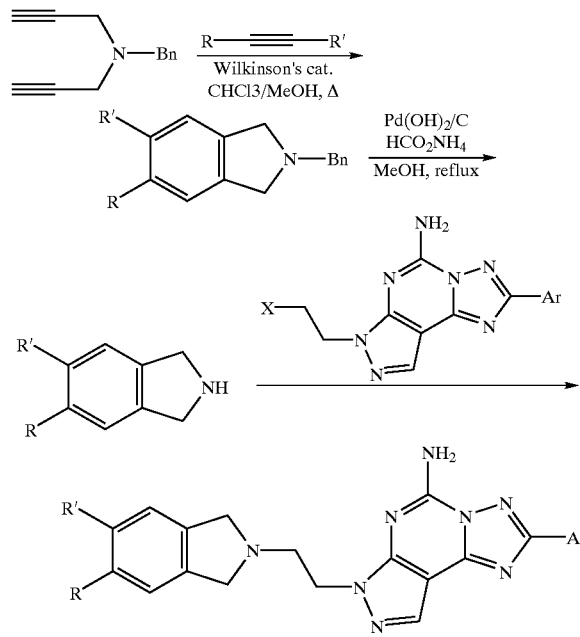

[2+2+2] cyclization of a diyne with an acetylene provides the benzyl protected isoindoline. Hydrogenolysis followed by displacement of a leaving group provides the desired final product.

SCHEME 4

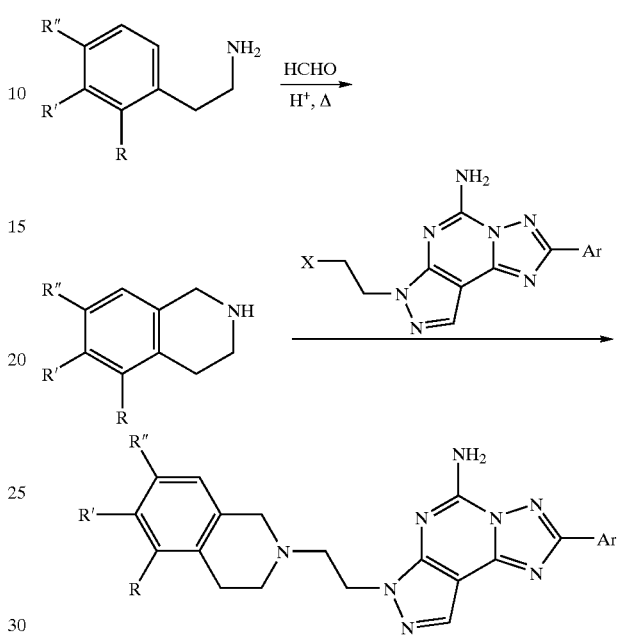

Pictet-Spengler cyclization of a phenethylamine gave a substituted tetrahydroisoquinoline. Displacement of a leaving group provided the desired final product.

EXAMPLES

The following examples serve to provide further appreciation of the invention, but are not meant in any way to restrict the effective scope of the invention. Side chains for compounds 29, 41, 44, 45, 47 and 49 were prepared as described in J. Heterocycl. Chem. 1971, 8, 779. Side chains for compounds 56 and 57 were purchased from Acros Organics USA, A Division of Fisher Scientific Company, 500 American Road, Morris Plains, N.J. 07950.

Example 1

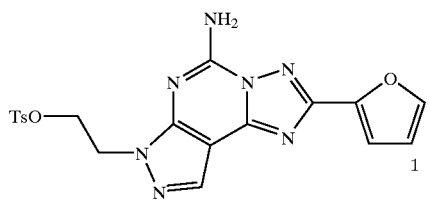

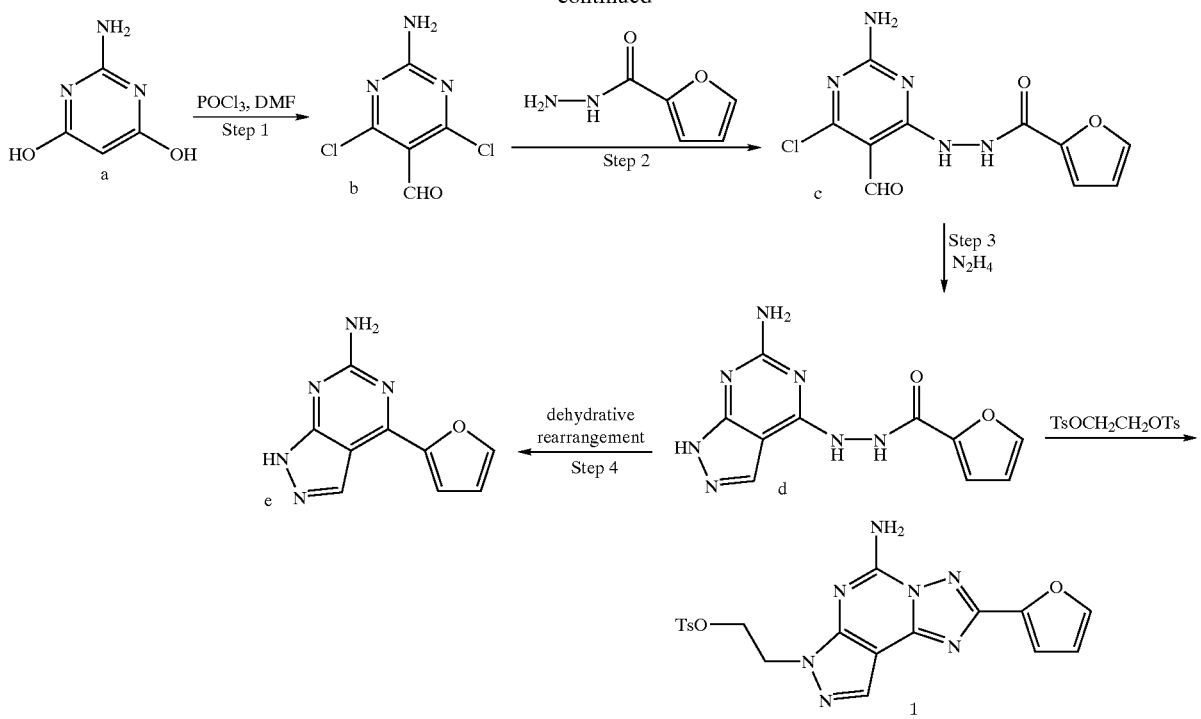

Step 1: Stir POCl₃ (84 ml, 0.9 mol) and chill to 5–10° C. while adding DMF (17.8 ml, 0.23 mol) drop-wise. Allow the mixture to warm to room temperature (RT) and add 2-amino-4,6-dihydroxypyrimidine (a) (14 g, 0.11 mol) portion-wise. Heat at 100° C. for 5 h. Strip off excess POCl₃ under vacuum, pour the residue into ice water, and stir overnight. Collect solids by filtration and recrystallize the dried material from a filtered ethyl acetate (EtOAc) solution to give the aldehyde, (b), m.p. 230° (dec). Mass spectrum: M+=192. PMR (DMSO): δ 8.6(δ, 2H); δ 10.1(s, 1H).

Step 2: Stir a mixture of the product of Step 1 (0.38 g, 2 mmol) and 2-furoic hydrazide (0.31 g, 2.5 mmol) in CH₃CN (50 ml) containing N,N-diisopropylethylamine (0.44 ml, 2.5 mmol) overnight at RT. Solvent strip the reaction mixture, and partition the residue between EtOAc and water. Dry the organic layer over MgSO₄, remove the solvent, and recrystallize the residue from CH₃CN to give the desired compound (c). Mass spectrum: MH+=282.

Step 3: Add hydrazine hydrate (75 mg, 1.5 mmol) to a hot CH₃CN solution of the product of Step 2 (0.14 g, 0.5 mmol). Reflux 1 h. Cool to RT and collect the product (d). Mass spectrum: MH+=260.

Step 4: Heat the product of Step 3 (5.4 g, 0.021 mol) in a mixture of hexamethyl-disilazine (100 ml) and N,O-bis (trimethylsilyl) acetamide (35 ml) at 120° C. overnight. Remove volatiles under vacuum and slurry the residue in hot water to give a solid precipitate. Recrystallize from 80% aqueous acetic acid to give the title compound. M.P.>300° C. Mass spectrum: MH+=242.

Step 5: Combine the product of Step 4 (6.0 g, 25 mmol), ethylene glycol ditosylate (11.1 g, 30 mmol), and NaH (60% in oil, 1.19 g, 30 mmol) in dry DMF (30 ml). Stir under N₂ for 24 h and filter to obtain compound 1 as a solid (PMR in DMSO: δ 4.47+4.51 triplets, 8.03s). Isolate additional material by chromatography of the filtrate.

Example 2

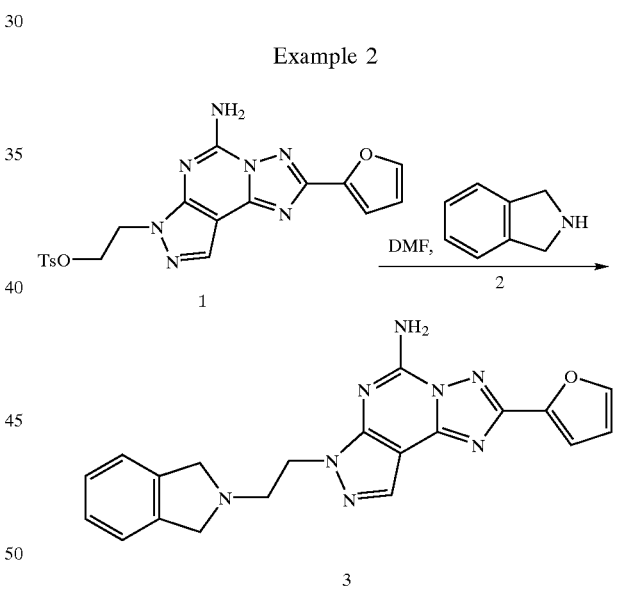

To a solution of compound 1 (0.34 mmol) in dry DMF (6.0 mL), isoindoline 2 (0.85 mmol) was added and the solution was stirred at 90° C. for 16 h. Isoindoline 2 was purchased from Acros Organics. The reaction mixture was cooled to room temperature and the solvent was removed under reduced pressure. To the residue, water (20 mL) was added, which was extracted with methylene chloride (3×35 mL), and washed with brine (15 mL). The combined organic extracts were dried (K₂CO₃), filtered, and the filtrate was concentrated in vacuo. The residue was purified by column chromatography on silica gel by eluting with 5% MeOH—CH₂Cl₂ to furnish the desired compound 3.

¹H NMR (400 MHz, DMSO-d6): δ 8.16 (s, 1H), 8.12 (bs, 2H), 7.94 (s, 1H), 6.72 (m, 1H), 7.12–7.21 (m, 5H), 4.41 (t,

2H), 3.90 (s, 4H), 3.15 (t, 2H); MS (LRMS) calcd for $C_{20}H_{18}N_8O$ 386, found m/z (M+H) 387.

Example 3

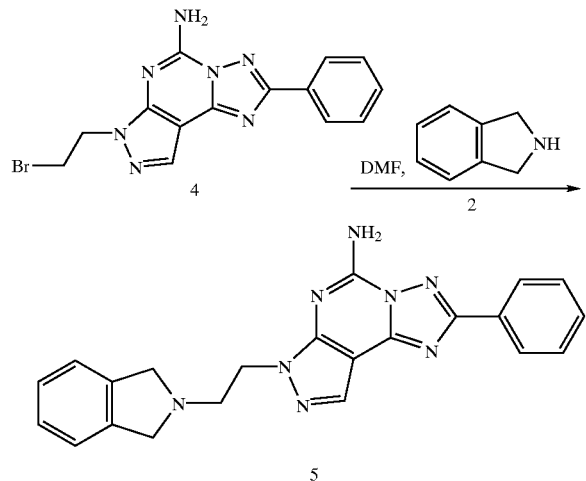

To a solution of compound 4 (0.42 mmol) in dry DMF (6.0 mL), isoindoline 2 (1.05 mmol) was added and the solution was stirred at 90° C. for 16 h. Compound 4 was made using a procedure similar to that for making compound 1 in example 1. Isoindoline 2 was purchased from Acros Organics. The reaction mixture was cooled to room temperature and the solvent was removed under reduced pressure. To the residue, water (20 mL) was added, which was extracted with methylene chloride (3×35 mL), and washed with brine (15 mL). The combined organic extracts were dried ($K_2CO_3$), filtered, and the filtrate was concentrated in vacuo. The residue was purified by column chromatography on silica gel by eluting with 5% MeOH—$CH_2Cl_2$ to furnish the desired compound 5.

$^1$H NMR (400 MHz, DMSO-d6): δ 8.21 (m, 2H), 8.19 (s, 1H), 8.08 (bs, 2H), 7.52 (m, 3H), 7.14–7.17 (m, 4H), 4.42 (t, 2H), 3.90 (s, 4H), 3.2 (t, 2H); MS (LRMS) calcd for $C_{22}H_{20}N_8$ 396, found m/z (M+H) 397.

Example 4

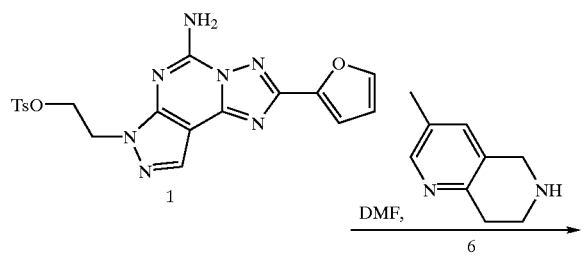

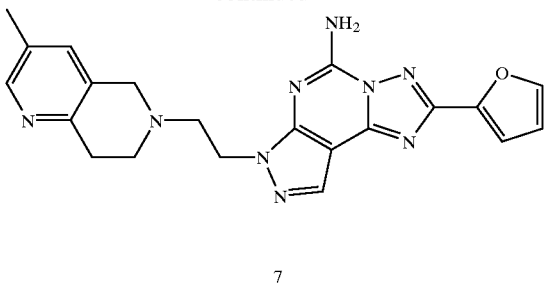

To a solution of compound 1 (0.34 mmol) in dry DMF (6.0 mL), 3-methyl-5,6,7,8-tetrahydro-1,6-naphthyridine 6 (0.85 mmol) was added and the solution was stirred at 90° C. for 16 h. The synthesis of 3-methyl-5,6,7,8-tetrahydro-1,6-naphthyridine 6 is described in Chem. Pharm. Bull. 1984, 32, 2522, the contents of which are incorporated by reference. The reaction mixture was cooled to room temperature and the solvent was removed under reduced pressure. To the residue, water (20 mL) was added, which was extracted with methylene chloride (3×35 mL), and washed with brine (15 mL). The combined organic extracts were dried ($K_2CO_3$), filtered, and the filtrate was concentrated in vacuo. The residue was purified by column chromatography on silica gel by eluting with 5% MeOH—$CH_2Cl_2$ to furnish the desired compound 7.

$^1$H NMR (400 MHz, DMSO-d6): δ 8.15 (s, 1H), 8.11 (s, 1H), 8.10 (bs, 2H), 7.95 (s, 1H), 7.21 (d, 2H), 6.72 (s, 1H), 4.43 (t, 2H), 3.61 (s, 2H), 2.94 (t, 2H), 2.74–2.82 (m, 4H), 2.18 (s, 3H); MS (LRMS) calcd for $C_{21}H_{21}N_9O$ 415, found m/z (M+H) 416.

Example 5

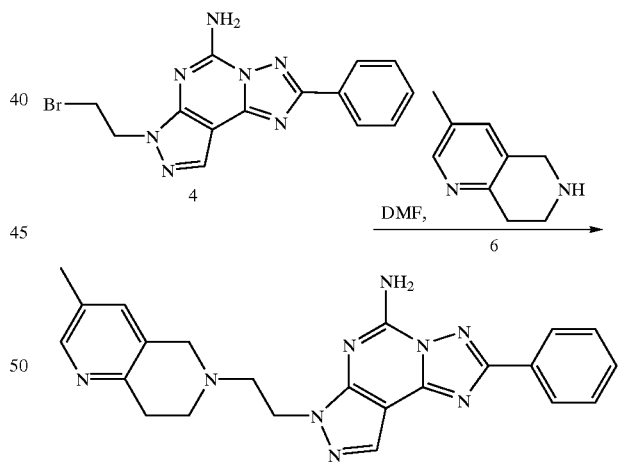

To a solution of compound 4 (0.42 mmol) in dry DMF (6.0 mL), 3-methyl-5,6,7,8-tetrahydro-1,6-naphthyridine 6 (1.05 mmol) was added and the solution was stirred at 90° C. for 16 h. The synthesis of 3-methyl-5,6,7,8-tetrahydro-1,6-naphthyridine 6 is described in Chem. Pharm. Bull. 1984, 32, 2522, the contents of which are incorporated by reference. The reaction mixture was cooled to room temperature and the solvent was removed under reduced pressure. To the residue, water (20 mL) was added, which was extracted with methylene chloride (3×35 mL), and washed with brine (15 mL). The combined organic extracts were dried (K$_2$CO$_3$), filtered, and the filtrate was concentrated in vacuo. The residue was purified by column chromatography on silica gel by eluting with 5% MeOH—CH$_2$Cl$_2$ to furnish the desired compound 8.

$^1$H NMR (400 MHz, DMSO-d6): δ 8.21 (m, 2H), 8.18 (s, 1H), 8.12 (s, 1H), 8.02 (bs, 2H), 7.52 (m, 3H), 7.23 (s, 1H), 4.42 (t, 2H), 3.62 (s, 2H), 2.96 (t, 2H), 2.79–2.81 (m, 4H), 2.19 (s, 3H); MS (LRMS) calcd for C$_{23}$H$_{23}$N$_9$ 425, found m/z (M+H) 426.

Example 6

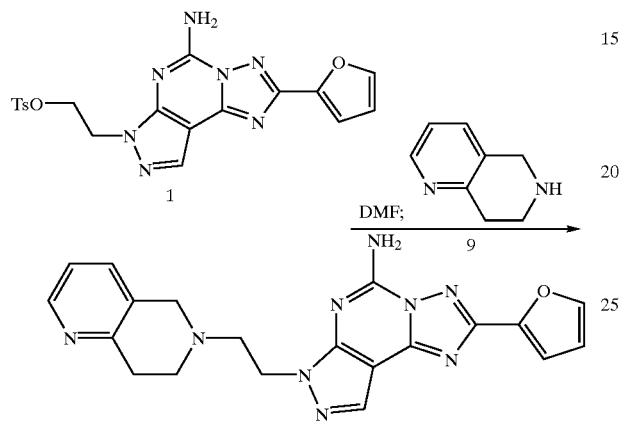

To a solution of compound 1 (0.15 g) in dry DMF (6.0 mL), 1,2,3,4-tetrahydro-1,6-naphthyridine 9 (0.85 mmol) was added and the solution was stirred at 90° C. for 16 h. The synthesis of 1,2,3,4-tetrahydro-1,6-naphthyridine 9 is described in *Chem. Pharm. Bull.* 1984, 32, 2522, the contents of which are incorporated by reference. The reaction mixture was cooled to room temperature and the solvent was removed under reduced pressure. To the residue, water (20 mL) was added, which was extracted with methylene chloride (3×35 mL), and washed with brine (15 mL). The combined organic extracts were dried (K$_2$CO$_3$), filtered, and the filtrate was concentrated in vacuo. The residue was purified by column chromatography on silica gel by eluting with 5% MeOH—CH$_2$Cl$_2$ to furnish the desired compound 10.

$^1$H NMR (400 MHz, DMSO-d6): δ 8.34 (d, 1H), 8.15 (s, 1H), 8.1 (bs, 2H), 7.93 (s, 1H), 7.42 (d, 1H), 7.21 (s, 1H), 7.12 (m, 1H), 6.72 (s, 1H), 4.42 (t, 2H), 3.66 (s, 2H), 2.98 (t, 2H), 2.81 (m, 4H); MS (LRMS) calcd for C$_{20}$H$_{19}$N$_9$O 401, found m/z (M+H) 402.

Example 7

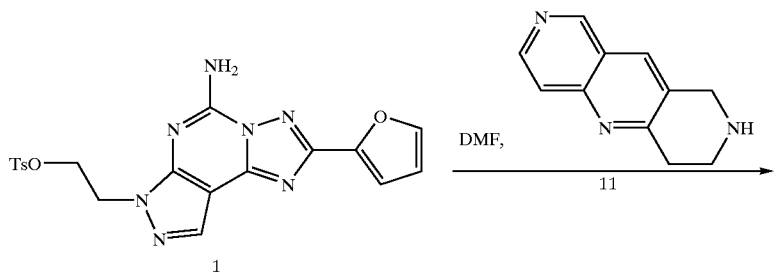

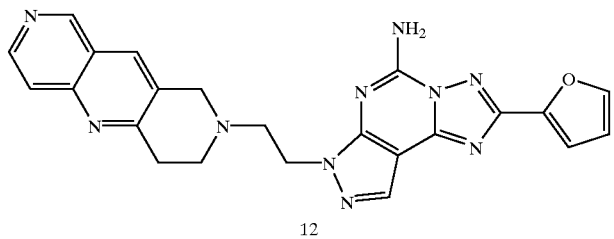

To a solution of compound 1 (0.34 mmol) in dry DMF (6.0 mL), 1,2,3,4-tetrahydropyrido-[4,3b]-[1,6]-naphthyridine 11 (0.85 mmol) was added and the solution was stirred at 90° C. for 16 h. 1,2,3,4-tetrahydropyrido-[4,3b]-[1,6]-naphthyridine 11 was purchased from Matrix Scientific. The reaction mixture was cooled to room temperature and the solvent was removed under reduced pressure. To the residue, water (20 mL) was added, which was extracted with methylene chloride (3×35 mL), and washed with brine (15 mL). The combined organic extracts were dried ($K_2CO_3$), filtered, and the filtrate was concentrated in vacuo. The residue was purified by column chromatography on silica gel by eluting with 5% MeOH—$CH_2Cl_2$ to furnish the desired compound 12.

$^1$H NMR (400 MHz, DMSO-d6): δ 9.23 (s, 1H), 8.59 (d, 1H), 8.20 (s, 1H), 8.16 (s, 1H), 8.08 (bs, 2H), 7.90 (s, 1H), 7.72 (d, 1H), 7.18 (s, 1H), 6.69 (m, 1H), 4.51 (t, 2H), 3.91 (s, 2H), 3.05 (m, 4H), 2.96 (t, 2H); MS (LRMS) calcd for $C_{23}H_{20}N_{10}O$ 452, found m/z (M+H) 453.

Example 8

The pharmacological activity of the compounds of the invention was determined by the following in vitro and in vivo assays to measure $A_{2a}$ receptor activity.

Human Adenosine $A_{2a}$ and $A_1$ Receptor Competition Binding Assay Protocol

Membrane Sources:

$A_{2a}$: Human $A_{2a}$ Adenosine Receptor membranes, Catalog #RB-HA2a, Receptor Biology, Inc., Beltsville, Md. Dilute to 17 μg/100 μl in membrane dilution buffer (see below).

Assay Buffers:

Membrane dilution buffer: Dulbecco's Phosphate Buffered Saline (Gibco/BRL)+10 mM $MgCl_2$.

Compound Dilution Buffer: Dulbecco's Phosphate Buffered Saline (Gibco/BRL)+10 mM $MgCl_2$ supplemented with 1.6 mg/ml methyl cellulose and 16% DMSO. Prepared fresh daily.

Ligands:

$A_{2a}$: [3H]-SCH 58261, custom synthesis, AmershamPharmacia Biotech, Piscataway, N.J. Stock is prepared at 1 nM in membrane dilution buffer. Final assay concentration is 0.5 nM.

$A_1$: [3H]-DPCPX, AmershamPharmacia Biotech, Piscataway, N.J. Stock is prepared at 2 nM in membrane dilution buffer. Final assay concentration is 1 nM.

Non-Specific Binding:

$A_{2a}$: To determine non-specific binding, add 100 nM CGS 15923 (RBI, Natick, Mass.). Working stock is prepared at 400 nM in compound dilution buffer.

$A_1$: To determine non-specific binding, add 100 μM NECA (RBI, Natick, Mass.). Working stock is prepared at 400 μM in compound dilution buffer.

Compound Dilution:

1 mM stock solutions of compounds in 100% DMSO were prepared. The compound was diluted in dilution buffer and then tested at 10 concentrations ranging from 3 μM to 30 pM. Working solutions were prepared at 4× final concentration in compound dilution buffer.

Assay Procedure:

Assays were performed in deep well 96 well plates. Total assay volume was 200 μl. Added was a 50 μl compound dilution buffer added (total ligand binding) or 50 μl CGS 15923 working solution ($A_{2a}$ non-specific binding) or 50 μl NECA working solution ($A_1$ non-specific binding) or 50 μl of drug working solution. Added was 50 μl ligand stock ([3H]-SCH 58261 for $A_{2a}$, [3H]-DPCPX for $A_1$). 100 μl of diluted membranes containing the appropriate receptor was added and the mixture was mixed. The mixture was incubated at room temperature for 90 minutes then harvested using a Brandel cell harvester onto Packard GF/B filter plates. 45 μl Microscint 20 (Packard) was added and counted using the Packard TopCount Microscintillation Counter. $IC_{50}$ values were determined by fitting the displacement curves using an iterative curve fitting program (Excel). Ki values were determined using the Cheng-Prusoff equation.

Haloperidol-induced Catalepsy in the Rat

Male Sprague-Dawley rats (Charles River, Calco, Italy) weighing 175–200 g were used. The cataleptic state was induced by the subcutaneous administration of the dopamine receptor antagonist haloperidol (1 mg/kg, sc), 90 min before testing the animals on the vertical grid test. For this test, the rats were placed on the wire mesh cover of a 25×43 plexiglass cage placed at an angle of about 70 degrees with the bench table. The rat was placed on the grid with all four legs abducted and extended ("frog posture"). The use of such an unnatural posture was essential for the specificity of this test for catalepsy. The time span from placement of the paws until the first complete removal of one paw (decent latency) was measured maximally for 120 sec.

The selective $A_{2A}$ adenosine antagonists under evaluation was administered orally at doses ranging between 0.03 and 3 mg/kg, 1 and 4 h before scoring the animals.

In separate experiments, the anticataleptic effects of the reference compound, L-DOPA (25, 50 and 100 mg/kg, ip), were determined.

6-OHDA Lesion of the Middle Forebrain Bundle in Rats

Adult male Sprague-Dowley rats (Charles River, Calco, Como, Italy), weighing 275–300 g, were used in all experiments. The rats were housed in groups of 4 per cage, with free access to food and water, under controlled temperature and 12 hour light/dark cycle. The day before the surgery the rats were fasted over night with water ad libitum.

Unilateral 6-hydroxydopamine (6-OHDA) lesion of the middle forebrain bundle was performed according to the method described by Ungerstedt et al. (*Brain Research*, 1971, 6-OHDA and Cathecolamine Neurons, North Holland, Amsterdam, 101–127), with minor changes. Briefly, the animals were anaesthetized with chloral hydrate (400 mg/kg, ip) and treated with desipramine (10 mpk, ip) 30 min prior to 6-OHDA injection in order to block the uptake of the toxin by the noradrenergic terminals. Then, the animals were placed in a stereotaxic frame. The skin over the skull is reflected and the stereotaxic coordinates (−2.2 posterior from bregma (AP), +1.5 lateral from bregma (ML), 7.8 ventral from dura (DV) were taken, according to the atlas of Pellegrino et al (Pellegrino L. J., Pellegrino A. S. and Cushman A. J., *A Stereotaxic Atlas of the Rat Brain*, 1979, New York: Plenum Press). A burr hole was then placed in the skull over the lesion site and a needle, attached to a Hamilton syringe, was lowered into the left MFB. Then 8 μg 6-OHDA-HCl was dissolved in 4 μl of saline with 0.05% ascorbic acid as antioxidant, and infused at the constant flow rate of 1 μl/1 min using an infusion pump. The needle was withdrawn after additional 5 min and the surgical wound was closed and the animals left to recover for 2 weeks.

Two weeks after the lesion the rats were administered with L-DOPA (50 mg/kg, ip) plus Benserazide (25 mg/kg, ip) and selected on the basis of the number of full contralateral turns quantified in the 2 h testing period by automated rotameters (priming test). Any rat not showing at least 200 complete turns/2 h was not included in the study.

Selected rats received the test drug 3 days after the priming test (maximal dopamine receptor supersensitivity).

The new $A_{2A}$ receptor antagonists were administered orally at dose levels ranging between 0.1 and 3 mg/kg at different time points (i.e., 1, 6, 12 h) before the injection of a subthreshold dose of L-DOPA (4 mpk, ip) plus benserazide (4 mpk, ip) and the evaluation of turning behavior.

We claim:

1. A compound having the structural formula A

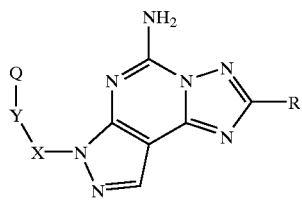

A or a pharmaceutically acceptable salt of said compound, wherein:

R is selected from the group consisting of $R^1$-furanyl-, $R^1$-thienyl-, $R^1$-pyridyl-, $R^1$-oxazolyl-, $R^1$-pyrrolyl- and $R^2$-aryl-;

X is —$(CH_2)_n$—;

Y is a pyrrolidinyl or azepanyl group with an aryl or heteroaryl moiety fused to two adjacent carbon atoms on Y, Y is a piperidinyl group with a pyridyl, pyrimidyl or pyrido[4,3-b]pyridyl group fused to two adjacent carbon atoms on Y, or Y is a piperidinyl group with a phenyl moiety fused to two adjacent carbon atoms on Y, wherein the piperidinyl group fused to a phenyl moiety has a substituent Q other than hydrogen, wherein X is attached to the N atom of the piperidinyl, pyrrolidinyl or azepanyl group;

Q is 1–4 substituents, which can be the same or different, and are independently selected from the group consisting of hydrogen, cycloalkyl, amino, aryl, aralkyl, heteroaryl, alkyl, $CF_3$, CN, halogen, $NO_2$, alkoxy, alkoxyalkoxy, cycloalkylalkoxy, alkylamino, alkylsulfonamino, alkylaminosulfonyl, dialkylaminosulfonyl, $NH_2SO_2$ and hydroxy;

n is 1 to 4;

$R^1$ is 1–3 substituents, which may be the same or different, and are independently selected from the group consisting of hydrogen, alkyl, $CF_3$, halogen and $NO_2$; and $R^2$ is 1–3 substituents, which may be the same or different, and are independently selected from the group consisting of hydrogen, alkyl, $CF_3$, halogen, $NO_2$, alkoxy, alkylamino, alkylsulfonamido, alkylaminosulfonyl, dialkylaminosulfonyl, aminosulfonyl, and hydroxyl.

2. A compound selected from the group consisting of

| COMPOUND # | STRUCTURE |
|---|---|
| 1 | 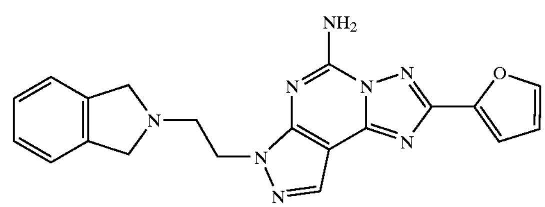 |
| 2 | 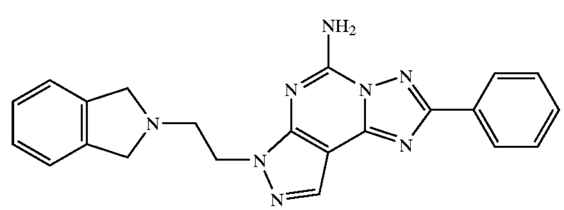 |
| 3 | 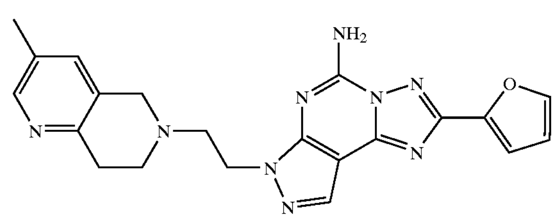 |
| 4 | 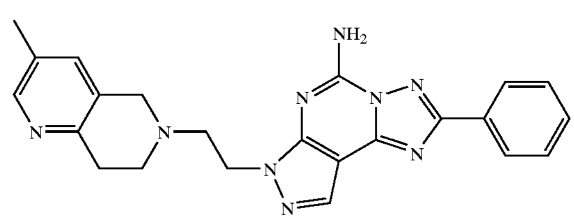 |

-continued

| COMPOUND # | STRUCTURE |
| --- | --- |
| 5 | 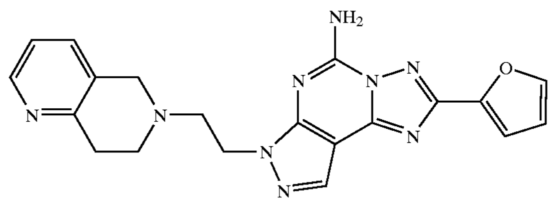 |
| 6 | 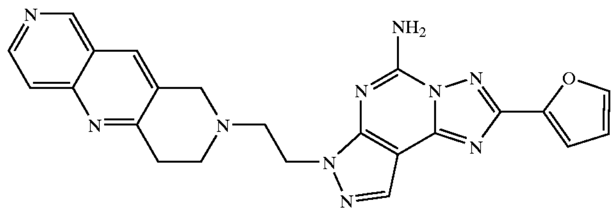 |
| 7 | 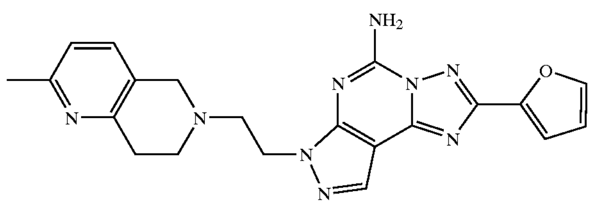 |
| 8 | 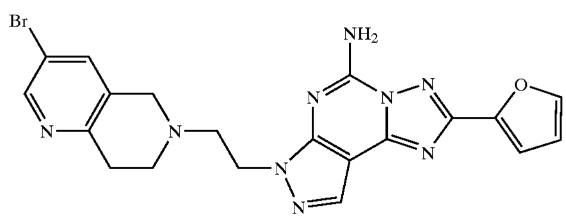 |
| 9 | 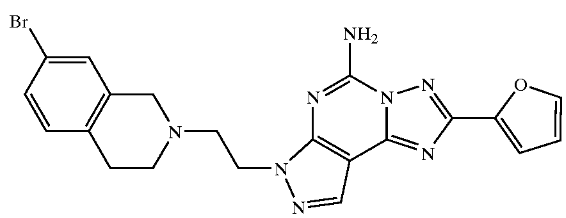 |
| 10 | 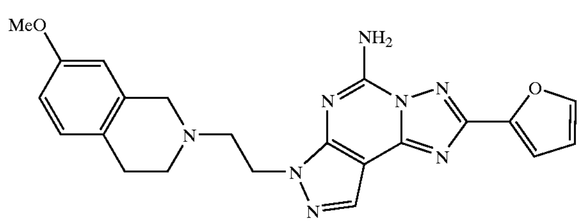 |
| 12 | 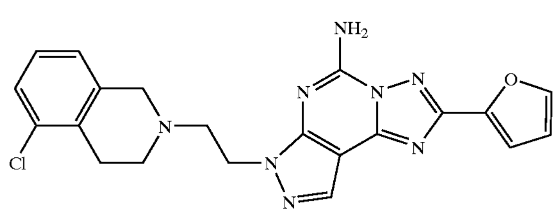 |

| COMPOUND # | STRUCTURE |
|---|---|
| 13 | 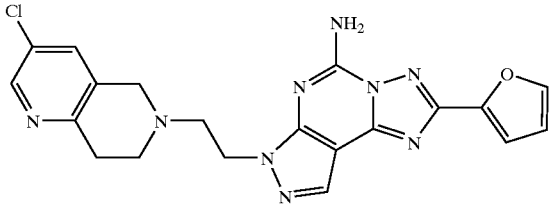 |
| 14 | 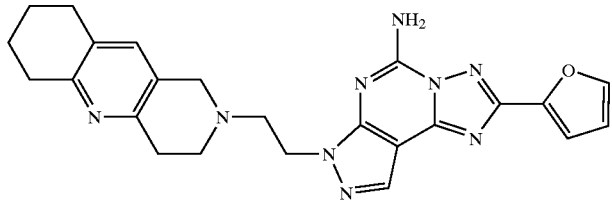 |
| 15 | 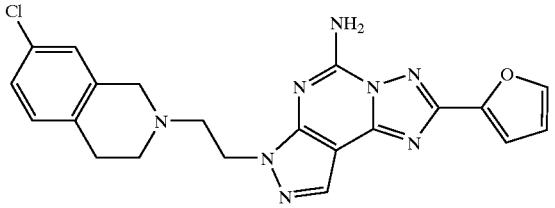 |
| 16 | 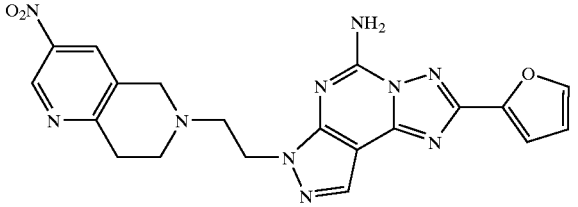 |
| 17 | 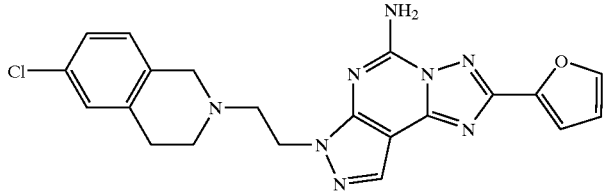 |
| 18 | 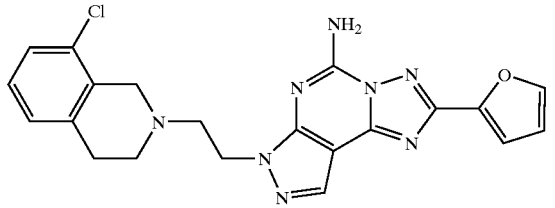 |
| 19 | 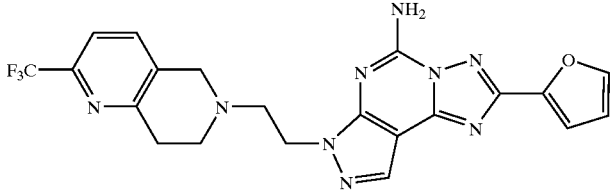 |

-continued

| COMPOUND # | STRUCTURE |
|---|---|
| 20 | 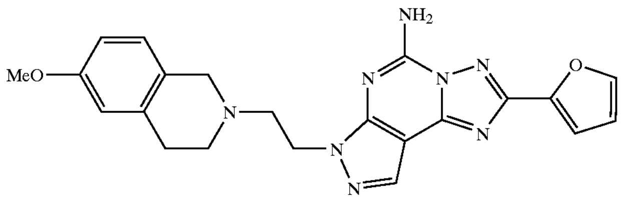 |
| 21 | 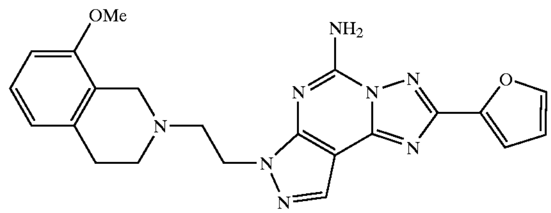 |
| 22 | 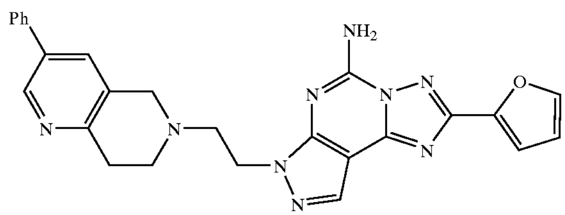 |
| 23 | 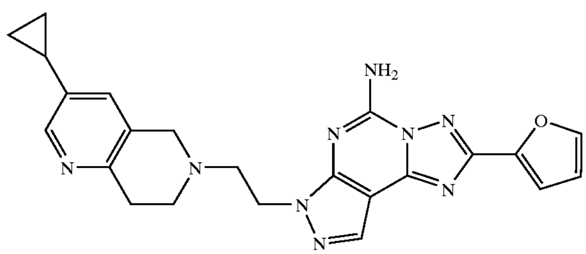 |
| 24 | 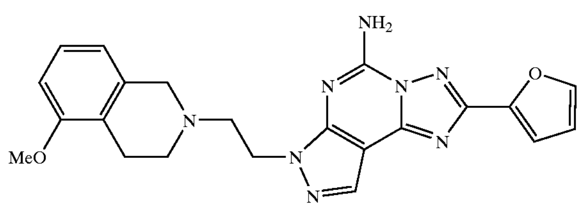 |
| 25 | 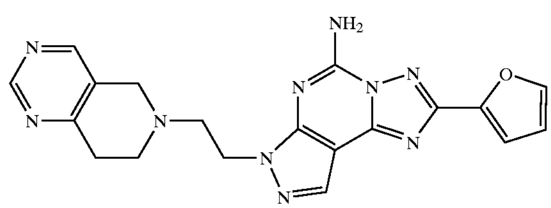 |
| 26 | 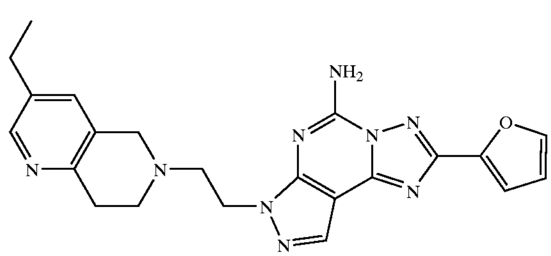 |

| COMPOUND # | STRUCTURE |
|---|---|
| 27 | 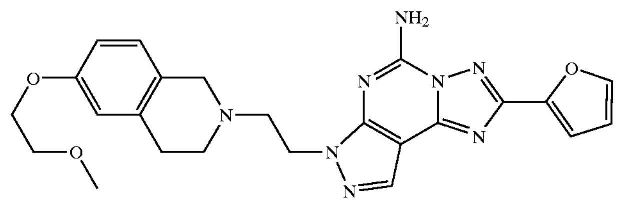 |
| 28 | 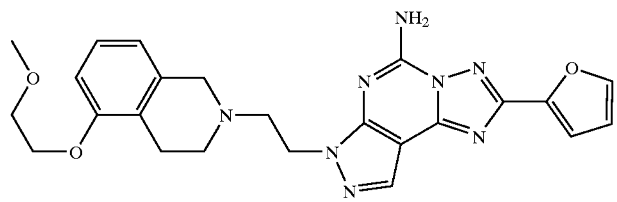 |
| 29 | 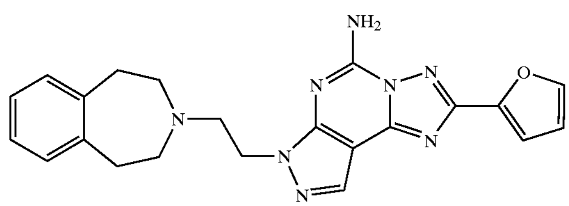 |
| 30 | 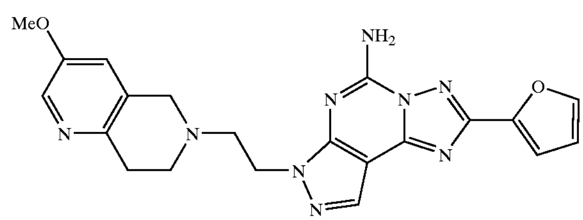 |
| 31 | 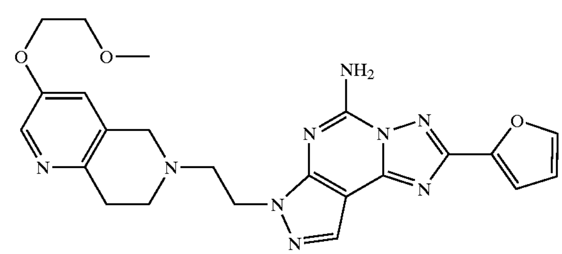 |
| 32 | 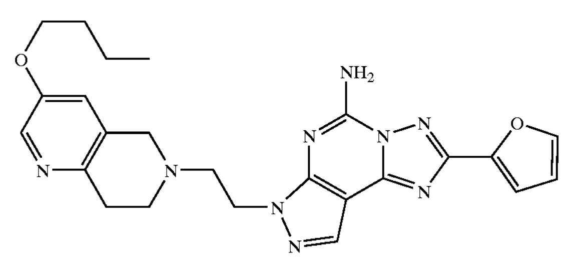 |

-continued
| COMPOUND # | STRUCTURE |
|---|---|
| 33 | 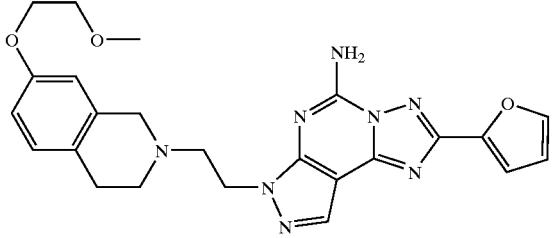 |
| 34 | 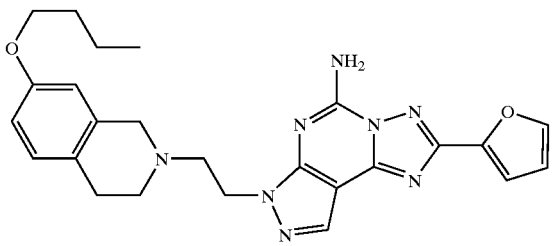 |
| 35 | 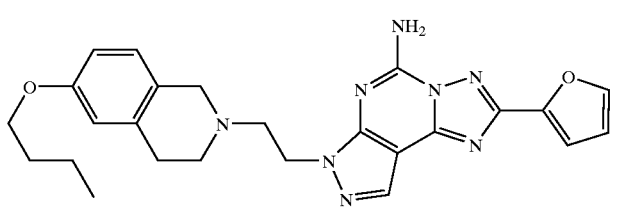 |
| 36 | 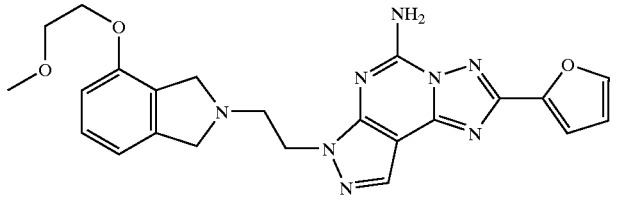 |
| 37 | 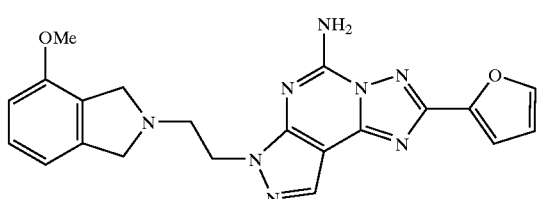 |
| 38 | 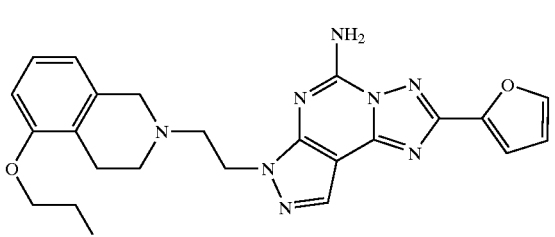 |
| 39 | 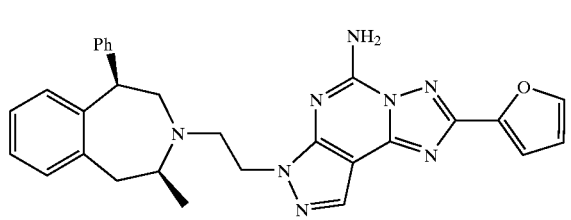 |

-continued
| COMPOUND # | STRUCTURE |
|---|---|
| 40 | 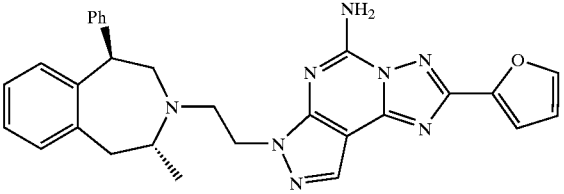 |
| 41 | 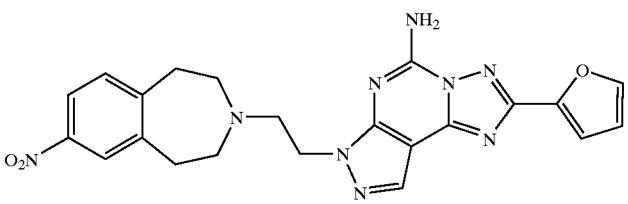 |
| 42 | 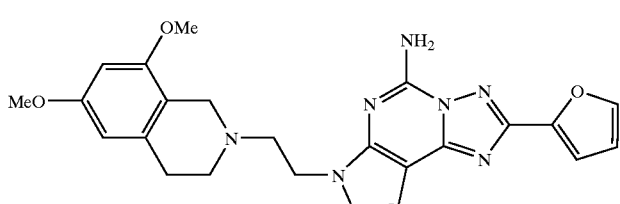 |
| 43 | 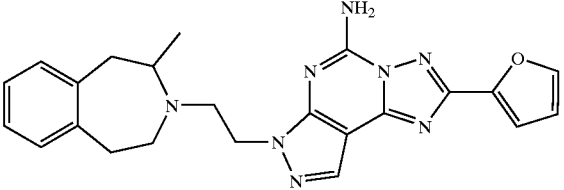 |
| 44 | 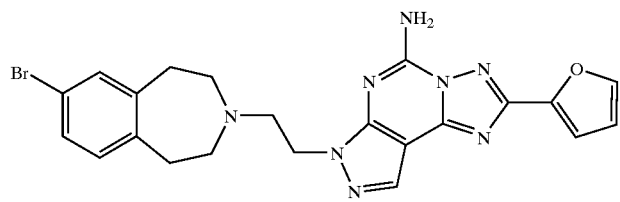 |
| 45 | 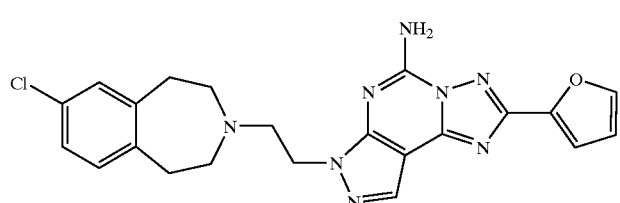 |
| 46 | 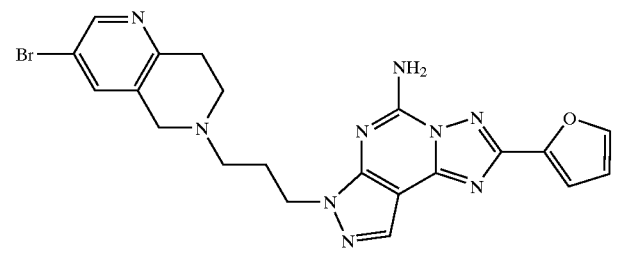 |

-continued
| COMPOUND # | STRUCTURE |
| --- | --- |
| 47 | 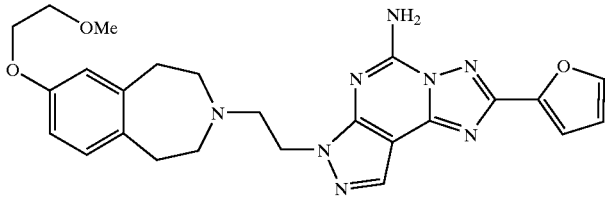 |
| 48 | 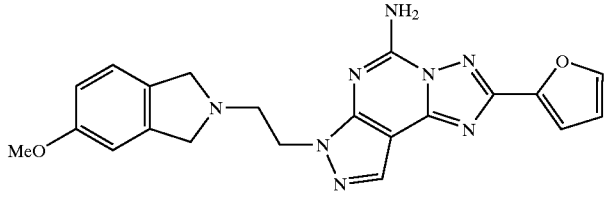 |
| 49 | 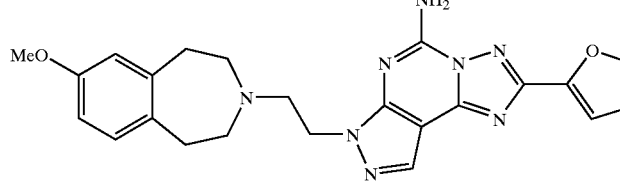 |
| 50 | 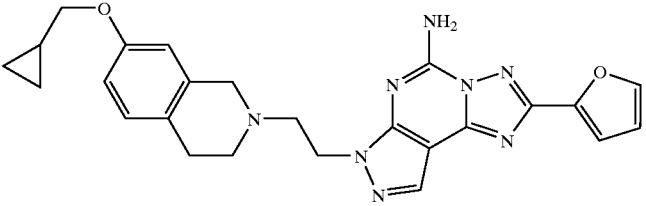 |
| 55 | 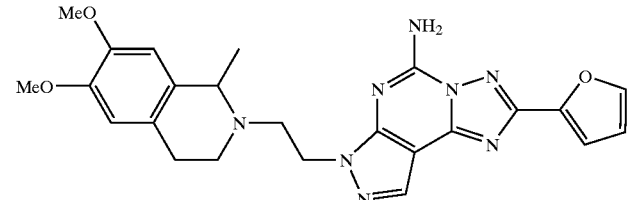 |
| 56 | 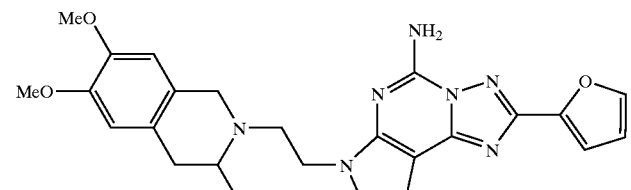 |
| 57 | 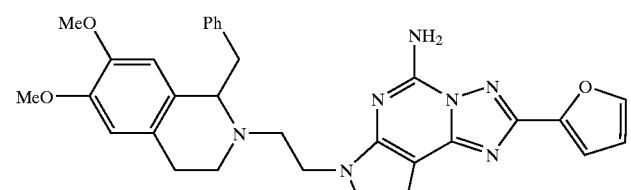 |

-continued
| COMPOUND # | STRUCTURE |
| --- | --- |
| 58 | 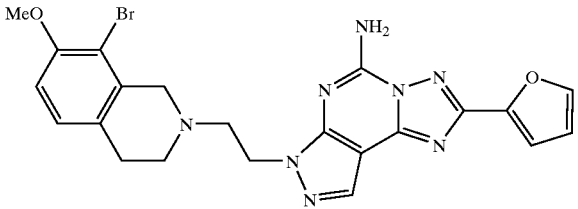 |
| | AND |
| 59 | 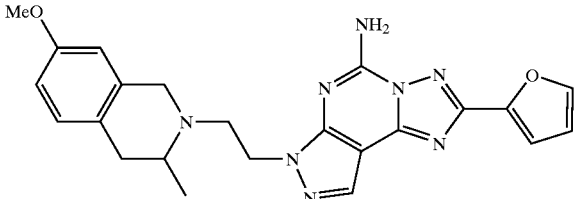 |
3. A compound according to claim 2 selected from the group consisting of:
| COMPOUND # | STRUCTURE |
| --- | --- |
| 1 | 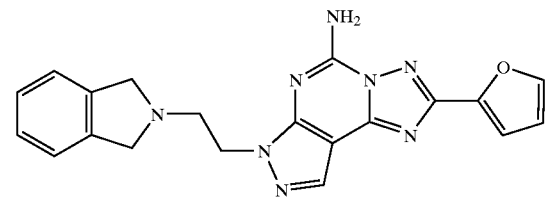 |
| 3 | 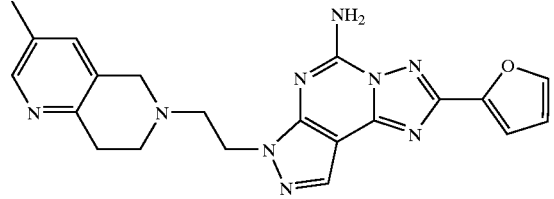 |
| 5 | 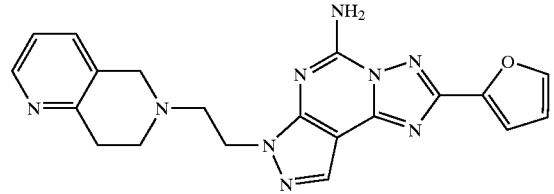 |
| 6 | 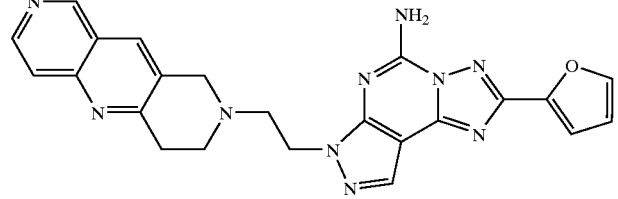 |

-continued

| COMPOUND # | STRUCTURE |
|---|---|
| 7 | 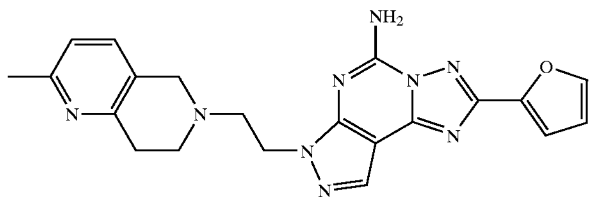 |
| 8 | 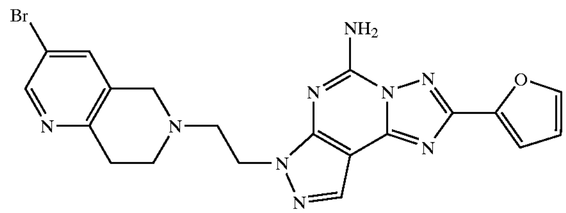 |
| 9 | 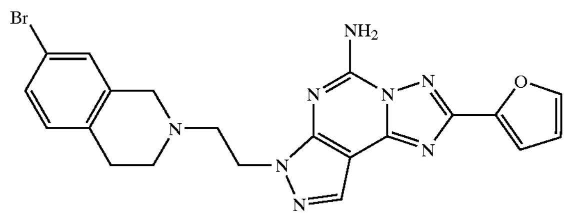 |
| 10 | 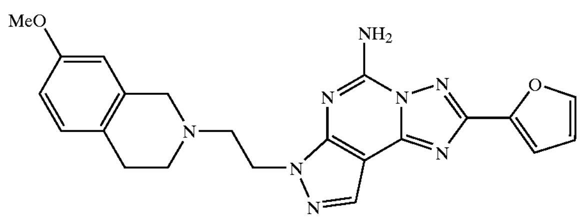 |
| 20 | 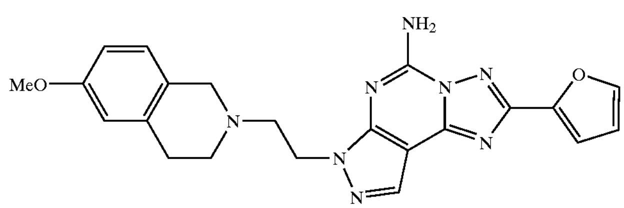 |
| 21 | 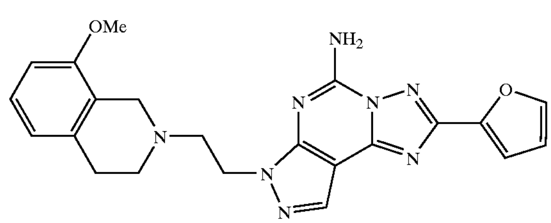 |
| 23 | 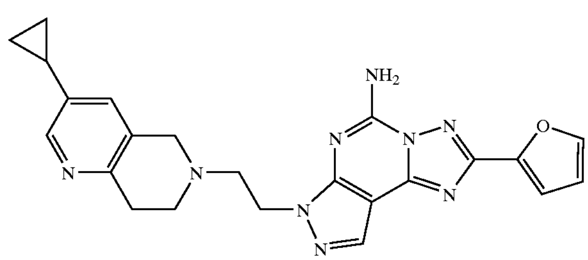 |

-continued
| COMPOUND # | STRUCTURE |
|---|---|
| 27 | 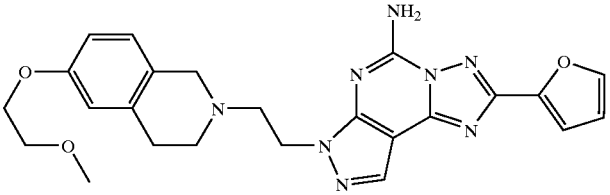 |
| 28 | 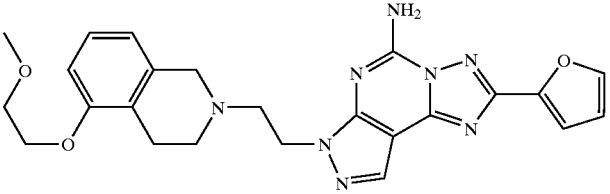 |
| 29 | 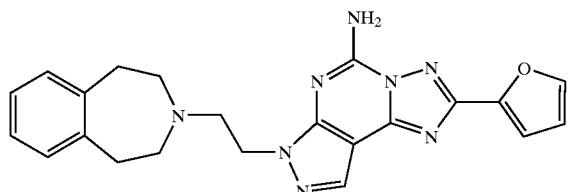 |
| 30 | 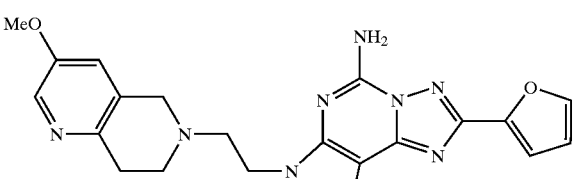 |
| 31 | 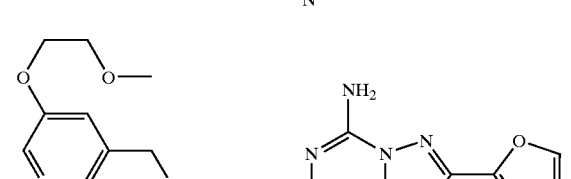 |
| 33 | 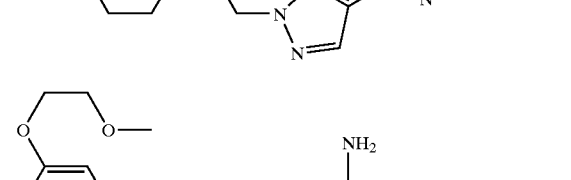 |
| 35 | 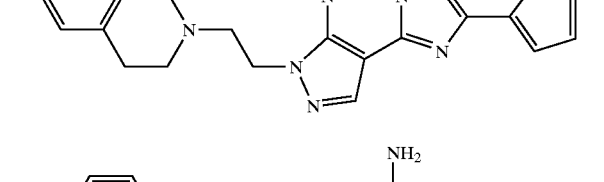 |

-continued
| COMPOUND # | STRUCTURE |
|---|---|
| 36 | 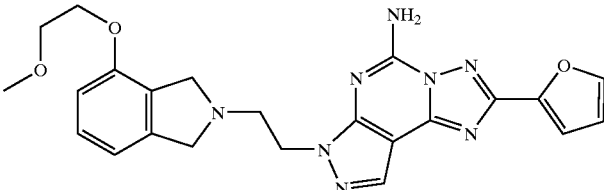 |
| 37 | 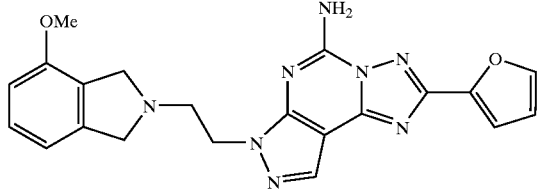 |
| 38 | 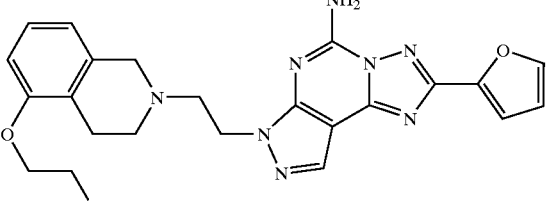 |
| 41 | 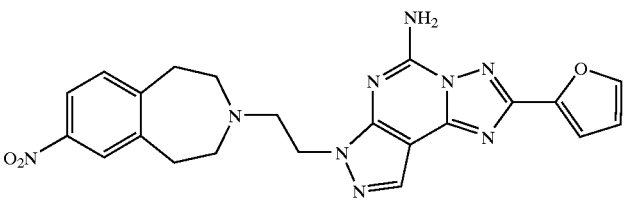 |
| 42 | 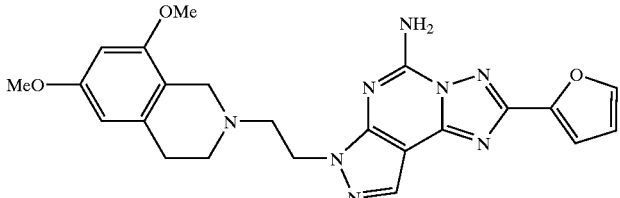 |
| 44 | 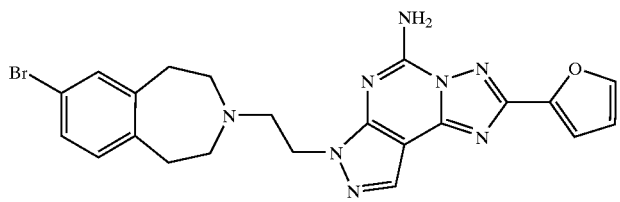 |
| 47 | 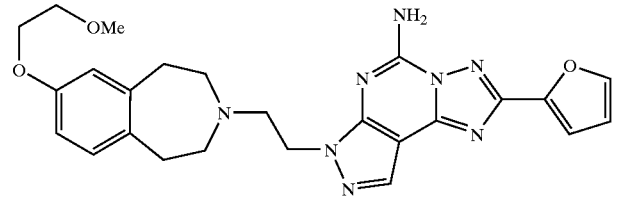 |

-continued

| COMPOUND # | STRUCTURE |
| --- | --- |
| 48 | 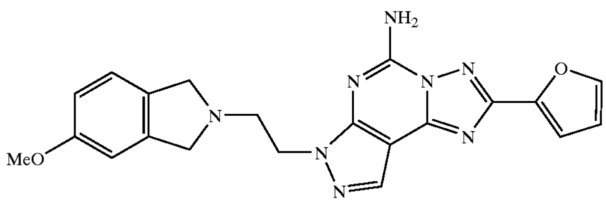 |
| 49 | 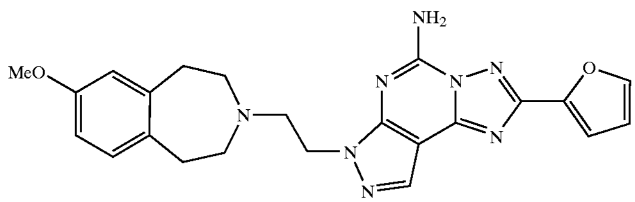 |
| 54 | 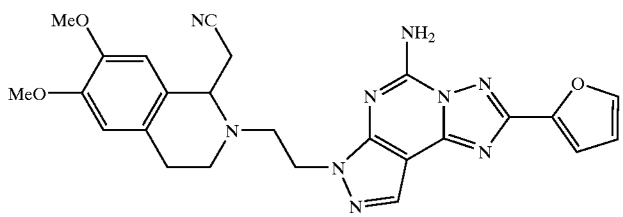 |
| 55 | 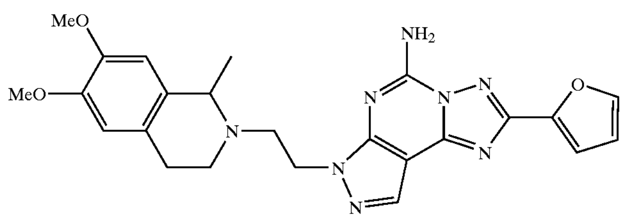 |
| 56 | 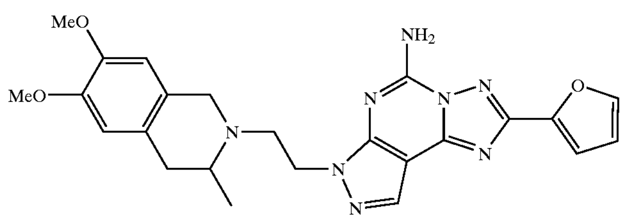 |
| 57 | 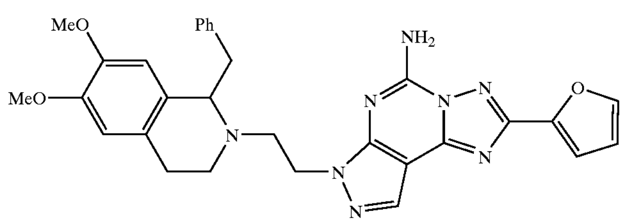 |
| 58 | 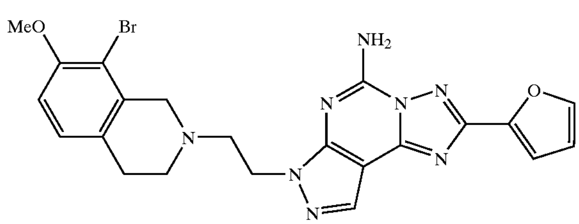 |

AND

-continued
| COMPOUND # | STRUCTURE |
|---|---|
| 59 | 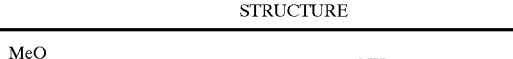 |
4. A compound according to claim 3 selected from the group consisting of:
| COMPOUND # | STRUCTURE |
|---|---|
| 3 | 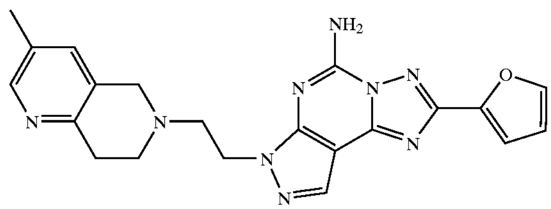 |
| 7 | 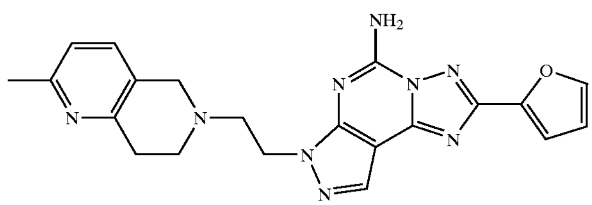 |
| 28 | 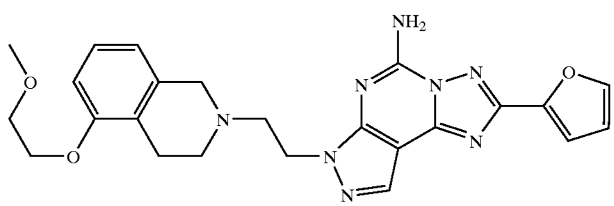 |
| 29 | 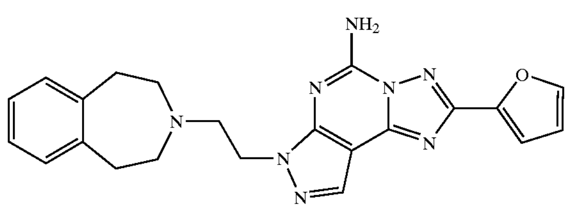 |
| 31 | 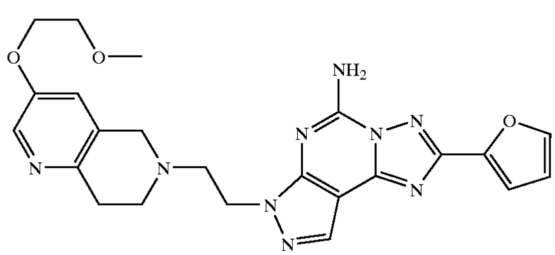 |

-continued
| COMPOUND # | STRUCTURE |
|---|---|
| 35 | 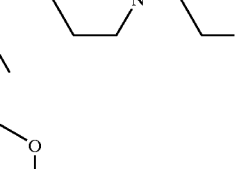 |
| 36 | 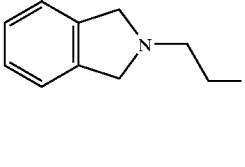 |
| 37 | 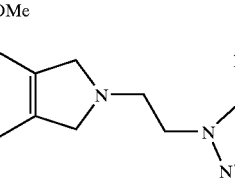 |
| 42 | 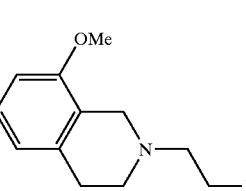 |
| 47 | 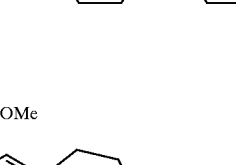 |
| 48 | 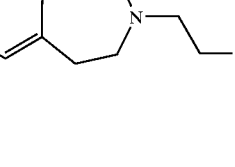 |
| 49 | 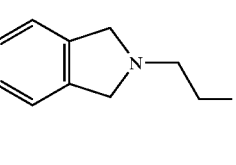 |

-continued
| COMPOUND # | STRUCTURE |
|---|---|
| 56 | 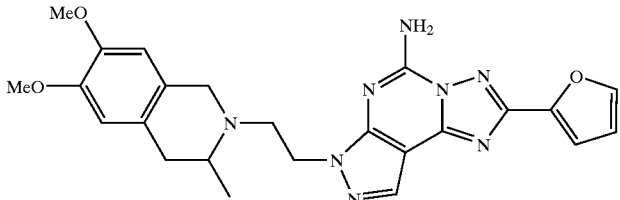 |
| 57 | 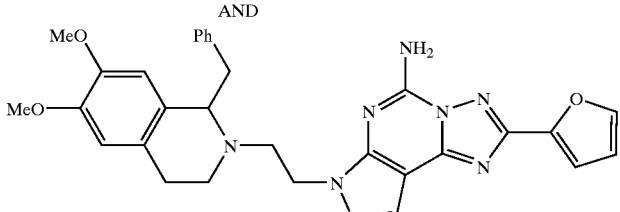 |
5. A compound according to claim 4 selected from the group of:
| COMPOUND # | STRUCTURE |
|---|---|
| 3 | 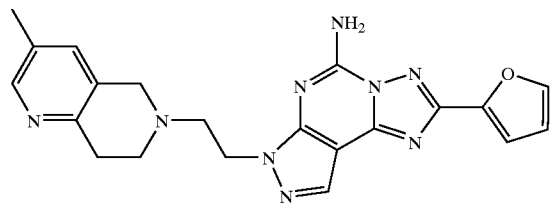 |
| 29 | 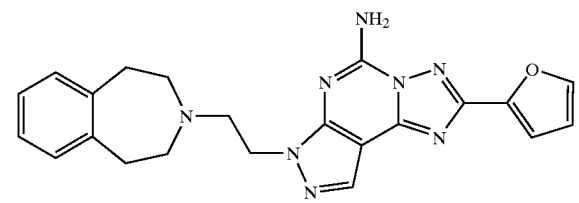 |
| 47 | 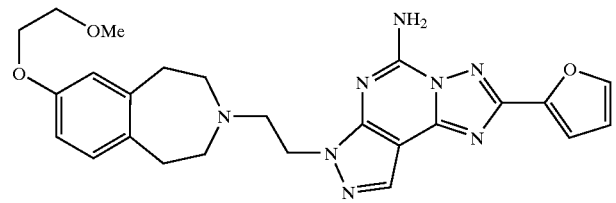 |
| 49 | 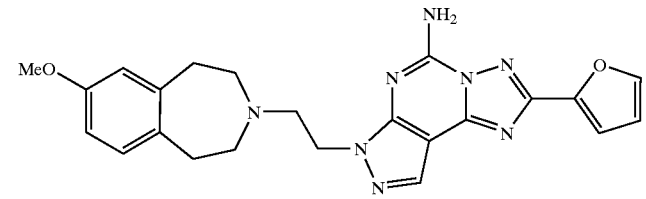 |

| COMPOUND # | STRUCTURE |
|---|---|
| 56 | 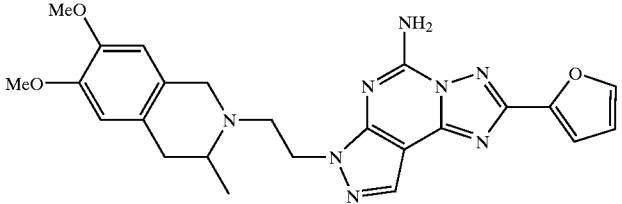 |
| | AND |
| 57 | 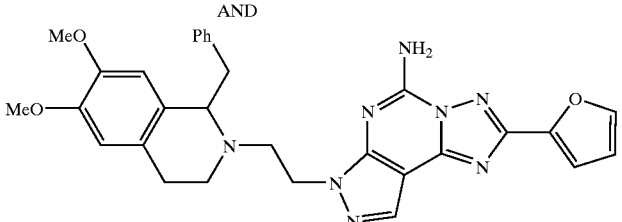 |

6. A pharmaceutical composition comprising one or more compounds of claim 1 and a pharmaceutically acceptable carrier.

7. The pharmaceutical composition according to claim 6, wherein the amount of compound or compounds of claim 1 is a therapeutically acceptable amount.

8. A method of treating psychoses, comprising administering one or more compounds of claim 1 to a patient in need of such treatment.

9. A compound having the structural formula A

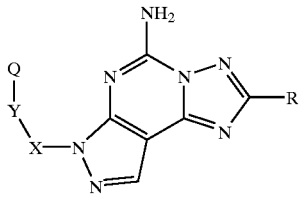

A or a pharmaceutically acceptable salt thereof, wherein:

R is furanyl;

X is —$(CH_2)_2$—;

Y is a pyrrolidinyl or azepanyl group with a phenyl moiety fused to two adjacent carbon atoms on Y; Y is a piperidinyl group with a pyridyl or pyrido[4,3-b]pyridyl group fused to two adjacent carbon atoms on Y; or Y is a piperidinyl group with a phenyl moiety fused to two adjacent carbon atoms on Y, wherein the piperidinyl group fused to the phenyl moiety has a substituent Q other than hydrogen; wherein X is attached to the N atom of the piperidinyl, pyrrolidinyl or azepanyl group; and Q is 1–4 substituents independently selected from the group consisting of hydrogen, cycloalkyl, aralkyl, alkyl, halogen, $NO_2$, alkoxy and alkoxyalkoxy.

* * * * *